(12) United States Patent
Oddo et al.

(10) Patent No.: US 11,826,512 B2
(45) Date of Patent: *Nov. 28, 2023

(54) MECHANICAL VENTILATOR WITH OXYGEN CONCENTRATOR

(71) Applicant: Aires Medical LLC., Ann Arbor, MI (US)

(72) Inventors: Nicholas Leonard Oddo, Hilton Head Island, SC (US); Shane Woody, Mooresville, NC (US); Chad Josey, Mooresville, NC (US); Dylan Moore, Mooresville, NC (US)

(73) Assignee: Aires Medical LLC., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/583,847

(22) Filed: Jan. 25, 2022

(65) Prior Publication Data
US 2022/0143353 A1 May 12, 2022

Related U.S. Application Data

(63) Continuation of application No. 16/996,062, filed on Aug. 18, 2020, now Pat. No. 11,229,763, which is a
(Continued)

(51) Int. Cl.
*A61M 16/00* (2006.01)
*A61M 16/10* (2006.01)
(Continued)

(52) U.S. Cl.
CPC ............ *A61M 16/101* (2014.02); *A61M 5/48* (2013.01); *A61M 16/0003* (2014.02);
(Continued)

(58) Field of Classification Search
CPC .. A61M 16/101; A61M 5/48; A61M 16/0003; A61M 16/0069; A61M 16/022;
(Continued)

(56) References Cited

U.S. PATENT DOCUMENTS 6,811,590 B2 * 11/2004 Lee ...................... B01D 53/047
96/115
10,500,359 B2 * 12/2019 Schwaibold .......... A61M 16/16
(Continued)

*Primary Examiner* — Frank M Lawrence, Jr.
(74) *Attorney, Agent, or Firm* — CALDWELL INTELLECTUAL PROPERTY LAW

(57) ABSTRACT

A ventilator, including an enclosure; a tubing configured to receive an input gas; a flow outlet airline in fluid communication with the tubing, wherein the flow outlet airline includes an airline outlet, and the flow outlet airline is configured to supply an output gas to a user via the airline outlet; a breath detection airline including an airline inlet, wherein the airline inlet is separated from the airline outlet of the flow outlet airline, and the breath detection airline is configured to receive breathing gas from the user during exhalation by the user via the airline inlet; a pressure sensor in direct fluid communication with the breath detection airline, wherein the pressure sensor is configured to measure breathing pressure from the user, and the pressure sensor is configured to generate sensor data indicative of breathing by the user.

17 Claims, 17 Drawing Sheets

Related U.S. Application Data continuation-in-part of application No. 16/704,413, filed on Dec. 5, 2019, now Pat. No. 10,946,161.

(60) Provisional application No. 63/047,742, filed on Jul. 2, 2020, provisional application No. 62/775,733, filed on Dec. 5, 2018.

(51) Int. Cl.

| | | |
|---|---|---|
| *A61M 16/20* | (2006.01) | |
| *A61M 16/12* | (2006.01) | |
| *F01L 1/00* | (2006.01) | |
| *F04D 9/04* | (2006.01) | |
| *A61M 5/48* | (2006.01) | |
| *A61M 25/00* | (2006.01) | |

(52) U.S. Cl.
CPC ...... *A61M 16/0069* (2014.02); *A61M 16/022* (2017.08); *A61M 16/12* (2013.01); *A61M 16/201* (2014.02); *F01L 1/00* (2013.01); *F04D 9/047* (2013.01); *A61M 2016/003* (2013.01); *A61M 2016/0027* (2013.01); *A61M 2016/1025* (2013.01); *A61M 2025/0002* (2013.01); *Y10S 425/106* (2013.01)

(58) Field of Classification Search
CPC ................ A61M 16/12; A61M 16/201; A61M 2016/0027; A61M 2016/003; A61M 2016/1025; A61M 2025/0002; A61M 16/0009; A61M 16/0066; A61M 16/0875; A61M 16/1045; A61M 16/1055; A61M 16/1065; A61M 16/16; A61M 16/203; A61M 16/208; A61M 2016/0021; A61M 2016/0039; A61M 2016/103; A61M 2205/07; A61M 2205/14; A61M 2205/18; A61M 2205/3368; A61M 2230/06; A61M 16/0051; A61M 16/024; A61M 16/0677; A61M 16/202; A61M 2205/3334; A61M 16/127; A61M 2202/0208; A61M 2205/3331; A61M 2205/3375; A61M 2205/502; A61M 2205/581; A61M 2205/8206; A61M 2205/825; A61M 2230/205; A61M 2230/30; F01L 1/00; F04D 9/047; Y10S 425/106; F04F 5/16; B01D 53/047; B01D 53/0473; B01D 53/04; B01D 53/0476; B01D 2253/108; B01D 2253/34; B01D 2256/12; B01D 2257/102
USPC ...................................... 95/130; 96/108, 121
See application file for complete search history.

(56) References Cited

U.S. PATENT DOCUMENTS

| | | | |
|---|---|---|---|
| 11,229,763 B2* | 1/2022 | Oddo | A61M 16/024 |
| 2015/0000664 A1* | 1/2015 | Desilva | A61M 16/12 |
| | | | 128/204.21 |
| 2015/0120067 A1* | 4/2015 | Wing | H02J 7/0048 |
| | | | 700/282 |
| 2017/0143932 A1* | 5/2017 | McCarthy | A61M 16/204 |
| 2018/0056024 A1* | 3/2018 | Harrington | A61M 16/161 |
| 2018/0344919 A1* | 12/2018 | Jones | G16Z 99/00 |
| 2020/0147338 A1* | 5/2020 | Lacey | A61M 16/208 |
| 2020/0188615 A1* | 6/2020 | Troili | A61M 16/12 |
| 2021/0386959 A1* | 12/2021 | Oddo | A61M 16/202 |
| 2022/0096781 A1* | 3/2022 | Dong | A61M 16/024 |
| 2022/0296846 A1* | 9/2022 | Liu | A61M 16/1075 |

\* cited by examiner

MECHANICAL VENTILATOR WITH OXYGEN CONCENTRATOR

CROSS-REFERENCE TO RELATED APPLICATIONS

This application claims priority, and the benefit of, U.S. patent application Ser. No. 16/996,062, filed Aug. 18, 2020, U.S. Provisional Patent Application 63/047,742, filed Jul. 2, 2020, U.S. patent application Ser. No. 16/704,413, filed on Dec. 5, 2019, which in turn claims priority, and the benefit of, U.S. Provisional Patent Application 62/775,733, filed on Dec. 5, 2018, each of which is hereby incorporated by reference in its entirety.

TECHNICAL FIELD

The present disclosure generally relates to a medical device, and more particularly, to a mechanical ventilator.

BACKGROUND

Conventional ventilators can lack portability and require continuous monitoring of user conditions and manual adjustment of ventilator settings by health care personnel. In many cases, expensive ventilation monitoring technologies such as CO2 capnography must be used in conjunction with a conventional ventilator, to determine effectiveness and make adjustments in settings during use. Conventional ventilator control methodology and ventilator configuration is not readily adaptable for ventilator use with certain user conditions, for example, when the user is talking, during sleep, or when the user is connected to Continuous Positive Airway Pressure (CPAP) and/or Bilevel Positive Airway Pressure (BiPAP) machines, for example, during sleep apnea therapy.

SUMMARY

A ventilator includes an enclosure, a tubing configured to receive an input gas, and a flow outlet airline in fluid communication with the tubing. The flow outlet airline includes an airline outlet. The ventilator further includes a breath detection airline including an airline inlet. The airline inlet is separated from the airline outlet of the flow outline airline. The ventilator further includes a pressure sensor in direct fluid communication with the breath detection airline. The ventilator includes a controller in electronic communication with the pressure sensor and an internal oxygen concentrator in fluid communication with the tubing. The internal oxygen concentrator is entirely disposed inside the enclosure.

A ventilator includes an enclosure, a tubing configured to receive an input gas, and a flow outlet airline in fluid communication with the tubing. The flow outlet airline includes an airline outlet. The flow outlet airline is configured to supply an output gas to a user via the airline outlet. The ventilator includes a breath detection airline including an airline inlet. The airline inlet is separated from the airline outlet of the flow outline airline. The breath detection airline is configured to receive breathing gas from the user during exhalation by the user via the airline inlet. The ventilator includes a pressure sensor in direct fluid communication with the breath detection airline. The pressure sensor is configured to measure breathing pressure from the user, and the pressure sensor is configured to generate sensor data indicative of breathing by the user. The ventilator includes a controller in electronic communication with the pressure sensor. The controller is programmed to detect the breathing by the user based on the sensor data received from the pressure sensor. The ventilator includes an internal oxygen concentrator in fluid communication with the tubing. The oxygen concentrator is entirely disposed inside the enclosure.

The above features and advantages and other features and advantages of the present teachings are readily apparent from the following detailed description of the modes for carrying out the present teachings when taken in connection with the accompanying drawings.

BRIEF DESCRIPTION OF THE DRAWINGS

The accompanying drawings, which are incorporated into and constitute a part of this specification, illustrate implementations of the disclosure and together with the description, serve to explain the principles of the disclosure.

FIG. 9B is a schematic cross-sectional view of the electronically controlled check valve of FIG. 9A in an open state.

FIG. 9C is a front view of a latch of the electronically controlled check valve of FIG. 9A.

DETAILED DESCRIPTION

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
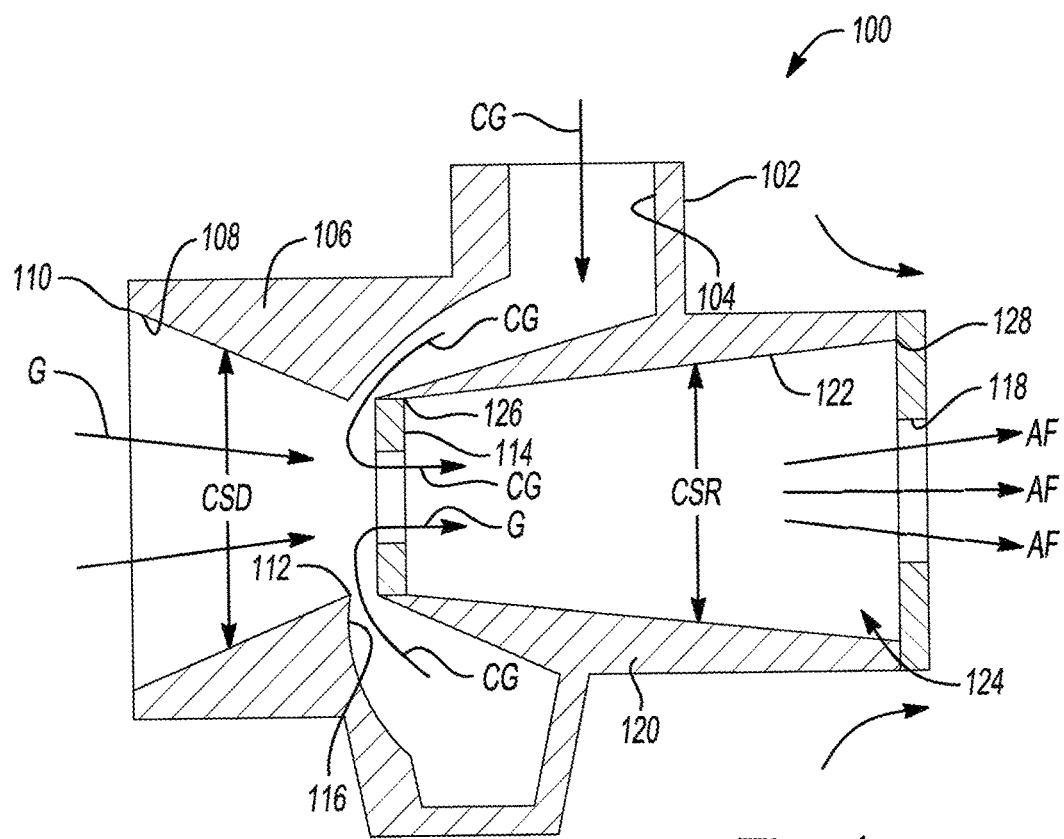
FIG. 1 is a schematic cross-sectional view of an adjustable air entrainment device using the Coanda effect.

FIG. 1 illustrates an adjustable air entrainment device 100 using the Coanda effect. The term "Coanda effect" means the tendency of a fluid jet to stay attached to a convex surface. The adjustable air entrainment device 100 includes a first inlet 102 configured to receive compressed air or oxygen (i.e., the compressed gas CG). The first inlet 102 defines a first annular chamber 104 to direct the flow of the compressed gas CG. In an embodiment that utilizes oxygen as the compressed gas CG entering through the first inlet 102, the adjustable air entrainment device 100 may be used to create a ventilation mode with variable/adjustable fraction of inspired oxygen ($FiO_2$) without the need for an air blower or air-$O_2$ mixing chamber. In other words, the adjustable air entrainment device 100 does not include an air blower or an air-$O_2$ mixing chamber.

The adjustable air entrainment device 100 further includes a second inlet 106 configured to receive air or oxygen (i.e., the gas G). The second inlet 106 defines a second annular chamber 108 in fluid communication with the first chamber 104 of the first inlet 102. The second inlet 106 includes a second annular chamber 108 that defines the second annular chamber 106. As a consequence, the inlet cross-sectional dimension CSD (e.g., inner diameter) of the second annular chamber 108 continuously decreases from a first inlet end 110 to a second inlet end 112 of the second inlet 106.

The adjustable air entrainment device 100 further includes a ring nozzle 114 configured to receive the compressed gas CG from the first inlet 102 and the gas G from the second inlet 106. Accordingly, the ring nozzle 114 is in fluid communication with the first inlet 102 and the second inlet 106. The ring nozzle 114 is configured to direct the flow of the compressed gas CG and the gas G and may be adjusted through a threaded or other screw type mechanism. As such, a gap 116 between the first annular chamber 104 of the first inlet 102 and the second annular chamber 108 of the second inlet 106 may be increased or decreased by the user or an electromechanical mechanism, thereby increasing or decreasing the amplification ratio of the air entrainment device 100. The ring nozzle 114 may be adjusted manually or automatically using an electromechanical mechanism. By adjusting the ring nozzle 114, the pressure drop is converted into amplified high velocity laminar flow. The diameter of the ring nozzle 114 may be increased or decreased through a screw type mechanism to further modify or adjust the air amplification ratio. The adjustable air entrainment device 100 may further include a bushing or nut/washer of a fixed diameter orifice in a straight bore tube. The bushing or nut/washer may be threaded along the diameter of an outlet 118, which would create an orifice restriction and hence reduce the amount of air entrainment depending on the diameter of the orifice.

The adjustable air entrainment device 100 further includes a device body 120 in fluid communication with the ring nozzle 114. The device body 120 includes a convex inner surface 122 defining a third annular chamber 124, thereby allowing the gas G and the compressed gas CG to flow through the ring nozzle 114 into the third annular chamber 124. The convex shape of the convex inner surface 122 of the device body 120 allows the adjustable air entrainment device 100 to use the Coanda effect. Therefore, the gas G and the compressed gas CG flowing into the third annular chamber 124 stays attached to the convex inner surface 122. The convex inner surface 122 of the device body 120 is tapered, thereby forming the convex shape of the convex inner surface 122. Specifically, the body cross-sectional dimension CSR (e.g., diameter) of the third annular chamber 124 continuously increases from a first body end 126 to a second body end 128 of the device body 120, thereby allowing the adjustable air entrainment device 100 to use the Coanda effect. Due to the use of the Coanda effect, the device body 120 may be referred to as an amplifier and is configured to amplify the airflow entering the adjustable air entrainment device 100.

The adjustable air entrainment device 100 further includes an outlet 118 in fluid communication with the third annular chamber 124 of the device body 120. The outlet 118 may be configured as an orifice and receives the airflow amplified by the device body 120. The amplified airflow AF may then exit the air entrainment device 100 through the outlet 118. Further, the airflow AF may be further amplified downstream of the outlet 118 by entraining additional air from the surroundings at the exit of the outlet 118.

During operation, compressed gas CG (e.g., compressed air or compressed oxygen) enters through the first annular chamber 104 of the first inlet 102 of the adjustable air entrainment device 100. Then, the compressed gas CG is throttled through the ring nozzle 114 at a high velocity and into the third annular chamber 124 of the device body 120. While in the third annular chamber 124, the airflow stays attached to the convex inner surface 122 of the device body 120, thereby creating a vacuum that induces air entrainment at the first inlet 102.

Figure 2:
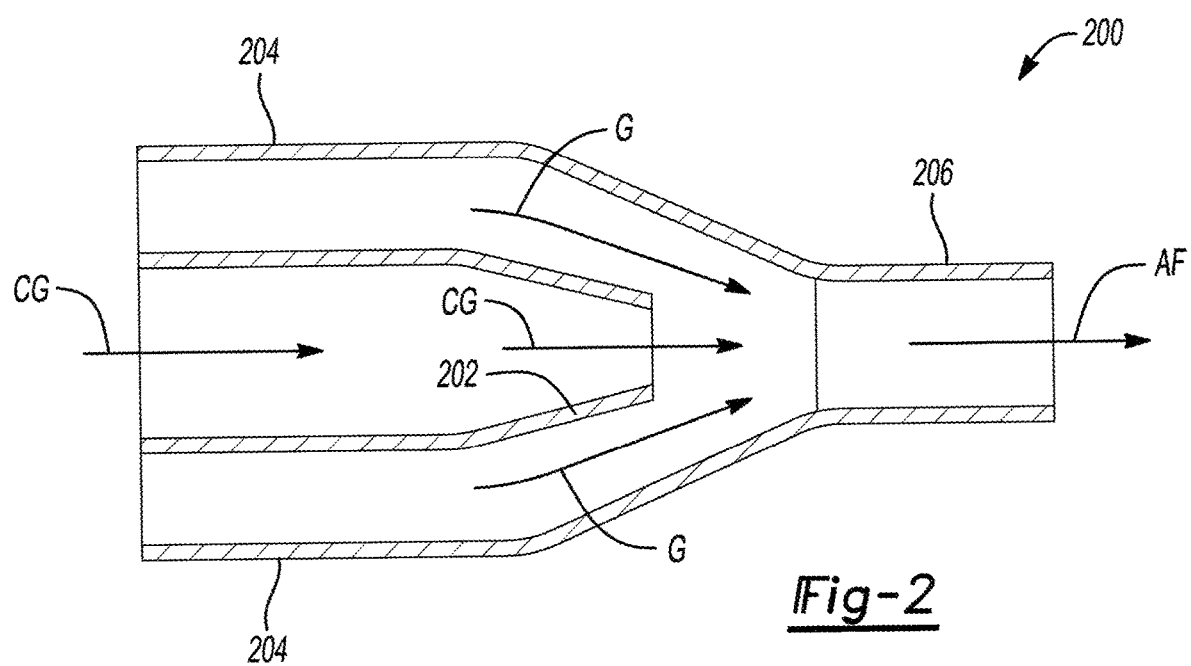
FIG. 2 is a schematic cross-sectional view of a fixed air entrainment device using the Jet Mixing Principle.
Figure 3:
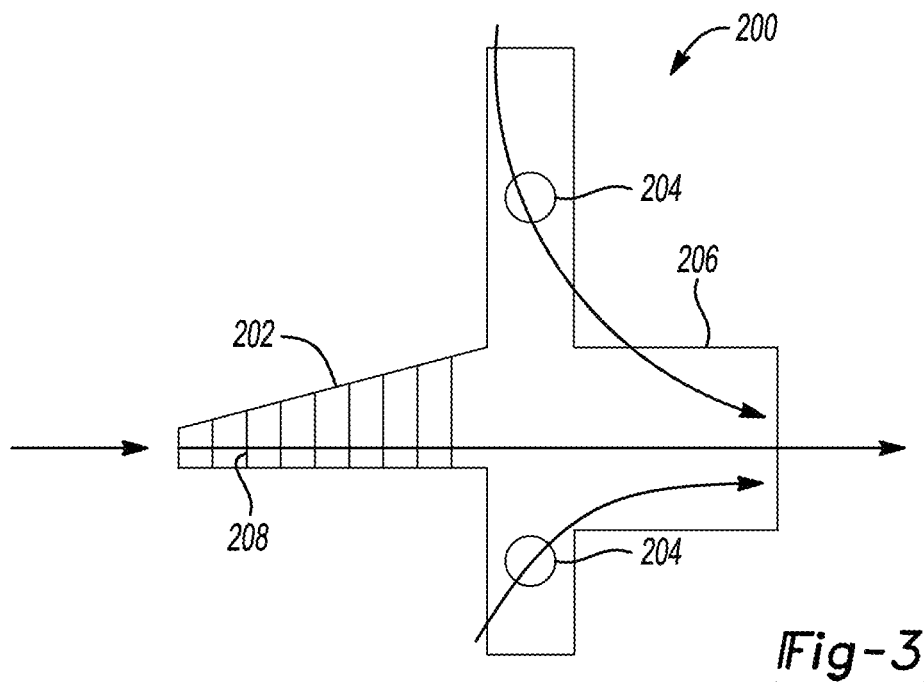
FIG. 3 is schematic illustration of a fixed air entrainment device that uses the Jet Mixing Principle.

With reference to FIGS. 2 and 3, a fixed air entrainment device 200 includes a funnel shaped tube 202 configured to receive compressed air or oxygen (i.e., compressed gas CG). Due to its funnel shape, the funnel shaped tube 202 creates a jet flow pattern. The fixed air entrainment device 200 further includes a plurality of air entrainment ports 204 in fluid communication with the funnel shaped tube 202. In addition, the fixed air entrainment device 200 further includes an outlet tube 206 in fluid communication with the funnel shape tube 202. Each of the air entrainment ports 204 is configured to entrain a unidirectional flow (i.e., gas G) of room air in a high-pressure zone by creating a low-pressure zone at the outlet tube 206. The oxygen or air flowing through the funnel shape tube 202 is ejected through the outlet tube 206 (see e.g., airflow AF). The ratio of air entrainment is mechanically designed based on several variables, such as air entrainment port size, the shape and/or diameter of the funnel shaped tube 202 for the oxygen gas source, and/or gaps between the funnel shaped tube 202 and the outlet tube 206.

As shown in FIG. 3, the funnel shaped tube 202 may be configured as an inlet hose including a plurality of barbs 208 to facilitate connection to an oxygen source. Additionally, the outlet tube 206 may be configured as a hose fitting to facilitate connection to a breathing tube. For example, the outlet tube 206 may be configured as a 22-millimeter diameter hose fitting to connect to and/or facilitate connection with a standard breathing tube, such as a continuous positive airway pressure (CPAP) tube or a single limb ventilator patient circuit.

During operation, the compressed air or oxygen (i.e., compressed gas) enters the funnel shaped tube 202 to create a jet flow pattern. The air entrainment ports 204 then entrain the unidirectional flow of room air (i.e., gas G) in a high-pressure zone by creating a low pressure zone at the outlet tube 206.

Figure 4:
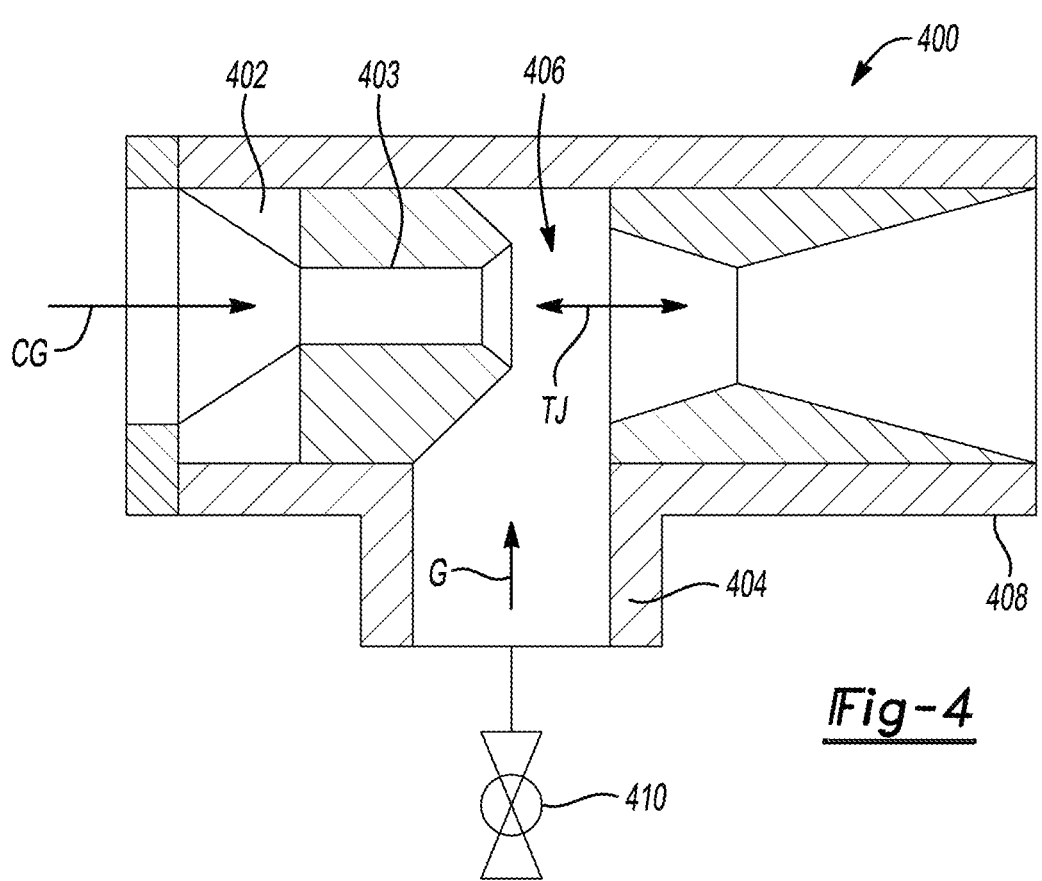
FIG. 4 is a schematic cross-sectional view of an air entrainment device that uses Venturi Vacuum with a manual valve to regulate the amount air entrainment.

With reference to FIG. 4, an adjustable air entrainment device 400 may use the Venturi effect. The adjustable air entrainment device 400 includes a funnel shaped inlet 402 configured to receive compressed air or oxygen (i.e., compressed gas CG). The adjustable air entrainment device 400 further includes a nozzle 404. During operation, the compressed air or oxygen (i.e., compressed gas CG) enters the funnel shaped inlet 402 and then flows through the nozzle 404 to create a jet flow pattern. The adjustable entrainment device 400 further includes an air gap 406 downstream of the nozzle 403 and an air entrainment port 404 in fluid communication with the nozzle 403. The air entrainment port 404 is configured to receive room air (i.e., gas G) at atmospheric pressure. The turbulent air jet TJ exiting the nozzle 403 entrains room air through the air gap 406 and serves as the "motive fluid flow" to pull or create a vacuum at the air entrainment port 404. The adjustable air entrainment device 400 further includes a mixer outlet 408 in fluid communication with the air gap 406. The mixer outlet 408 has a Venturi profile and is downstream of the air gap 406. The compressed air or oxygen (i.e., the compressed gas CG) plus entrained room air pulled using a Venturi vacuum is then exhausted through the mixer outlet 408. The adjustable air entrainment device 400 may include a manual or electrically actuated valve 410, which can be adjusted by a user or a machine to create an orifice restriction or vary the size of the air entrainment port 404, thereby allowing the user to increase or decrease the amount of air entrainment using the Venturi vacuum. Hence, the adjustable air entrainment device 400 may be used as a variable air entrainment device. Moreover, the air gap 406 and/or air entrainment port 404 may be increased or decreased using a slider mechanism (not shown), which can be used to affect the turbulence/velocity of the motive fluid flow/jet mixing profile as it enters the air gap 406, thereby increasing or decreasing the volume or flow rate of room air entrained via the Venturi vacuum effect.

Figure 5:
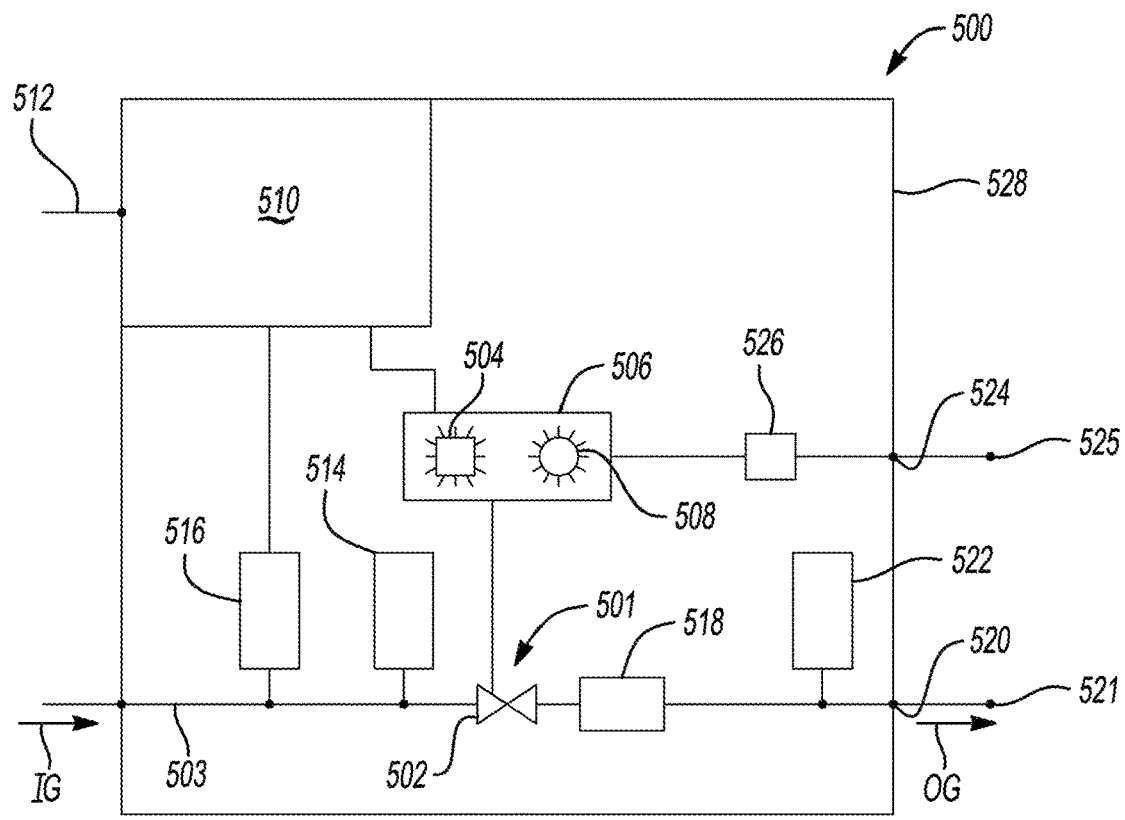
FIG. 5 is a schematic illustration of a ventilator with an on-off solenoid valve to modulate a compressed oxygen source.

With reference to FIG. 5, a ventilator 500 includes an on-off or electronically controlled solenoid valve 502 configured to modulate compressed oxygen or air sources. Accordingly, the solenoid valve 502 has at least an open state and a closed state. The solenoid valve 502 may be part of a valve arrangement 501. The valve arrangement 501 may therefore include one or more of the solenoid valves 502. It is also contemplated that the valve arrangement 501 may include other types of valves. Hence, the ventilator 500 may include a single solenoid valve 502 to minimize cost and weight. The ventilator 500 functions by receiving input gas IG from an input gas source through a ventilator tubing 503. As non-limiting examples, the input source may be an air compressor, air blower, stationary oxygen concentrator, portable oxygen concentrator, air tank, and/or oxygen tank. A continuous flow of input gas IG enters the ventilator 500 through the ventilator tubing 503, and when the solenoid valve 502 opens, the flow rate of input gas IG and output gas OG is the same or at least substantially the same.

The ON-OFF cycles of the solenoid valve 502 are controlled using a controller 504, such as a microprocessor or microcontroller unit. The controller 504 may be part of an electronic board 506, which can contain additional electronic components including but not limited to: power electronics, resistors, capacitors, alarms 508, and copper traces. The electronic board 506 may include one or more alarms 508. The alarms 508 can, for example, be used to warn the user of one or more of the following conditions: tubing disconnections, electrical or air supply failure, high peak airway pressure, auto-positive end-expiratory pressure (auto-PEEP), high gas supply pressures, and/or no spontaneous breathing. Further, this electronic board 506 may be utilized as a battery management system for a portable ventilator device that is battery powered.

The ventilator 500 can include an electrical power source 510, such as a portable rechargeable Li-Ion battery pack or another suitable portable battery assembly. The electrical power source 510 (e.g., battery pack) may include a recharging interface 512, such as a port or cable, thereby allowing the electrical power source 510 to be recharged. As non-limiting examples, the recharging interface 512 may be a Universal Serial Bus-C (USB-C), a USB, a micro-USB, or other charging interfaces. The electrical power source 510 may be electrically connected to the electric board 506 to supply electricity to the controller 504 and the alarms 508.

This controller 504 may be in the form of an field-programmable gate array (FPGA), a microcontroller (MCU), single board computer, application-specific integrated circuit (ASIC), programmable logic controller (PLC) on a chip, and/or other processing or computer hardware that can control the ON/OFF or OPEN/CLOSE cycles of a solenoid valve 502. The solenoid valve 502 may be controlled using fluidic chips or other non-conventional or pneumatic methods of valve control, such as air cylinder actuations. For example, an air cylinder or pressure actuator 514 and a check valve may replace the electronically controlled solenoid valve 502. As such, the cracking pressure of the check valve would be higher than the input gas source IG and can only be opened using an air cylinder or pressure actuator 514. The air cylinder or pressure actuator 514 may be electronically controlled to open at the beginning or end of the respiration cycle (i.e., at inhalation) to provide a ventilatory inspiratory positive airway pressure (IPAP) or positive end-expiratory pressure (PEEP). This can be beneficial in situations where very low-pressure oxygen or compressed air sources are used, and where miniature electronically controlled solenoid valves have small orifices, in some cases as small as 0.009 inches diameter, would not be effective. The miniature solenoid valves create significant orifice/flow restrictions that necessitate the use of high-pressure input gas sources, in the range of 25-50 pounds per square inch (PSI). Check valves, on the other hand, generally have much larger orifices, such as 0.75 inch diameter, in small size form factors compared to the electronically controlled valve counterparts. For example, a 7 mm orifice electronically controlled solenoid valve weighs about 1 pound and consumes approximately 13 W of power, which would make the ventilator device bulky. By contrast, the ventilator 500 including the miniature air cylinder or pressure actuator 514 can rival a miniature electronically controlled solenoid valve 502 in terms of weight and power consumption, while having larger orifices and allow the use of lower pressure gas sources than in other systems. Any numbers provided above or below are only examples and should not be interpreted as functional limitations of the presently disclosed ventilator.

The ventilator 500 may include an oxygen or air tank 516, which is configured as a pressure source to deliver pressurized oxygen to the patient for ventilatory support. The electrical power source 510 may be electrically connected to the oxygen tank 516 and the electric board 506. However, the ventilator 500 may be completely pneumatically powered. As such, a certain portion of the input gas IG may be used to drive an impeller, which would generate electrical energy that can power the controller 504 and other energy consuming components such as the solenoid valve 502. However, other oxygen and/or pressure sources can be utilized such as continuous flow oxygen concentrators or air compressors. Further, flow control software and the hardware of the solenoid valve 502 may be utilized such that gas sources with different pressure values can be interchanged while maintaining a consistent or dynamically adjusted controlled gas flow rate to the patient. A pressure actuator may be built into the portable ventilator 500, allowing a pulse dose oxygen concentrator to be utilized. This pressure actuator can periodically trigger a pulse dose oxygen conserver at a fixed rate, such as once every 4 seconds or 15 "breaths per minute". The pulse dose oxygen bursts would accumulate inside an air volume tank connected to or inside the ventilator 500. The ventilator 500 then outputs the oxygen pulse from the air volume tank in a manner that ventilatory support would be provided the patient. The ventilator 500 may have two modes of operation, namely: (1) an oxygen conserver mode; and 2) ventilator mode. The ventilator mode may also have ventilator submodes of operation. These ventilation submodes may be selected by the patient, physician, and/or manufacturer and may include assist control, tidal assist ventilation, and/or synchronized intermittent mandatory ventilation (SIMV). The pressurized output gas OG may be outputted in a plurality of different waveforms, such as descending ramp, ascending ramp, sinusoidal, and/or square wave form, among others. Further, these ventilator gas output waveforms and flow rates may be adjusted based on breathing airway pressure and/or flow measurements from a second lumen airline. In the presently disclosed ventilator 500, the flow control and breathing measurements are separately obtained via dual lumen airlines. This dual lumen airline setup prevents electrical signal interference and saturation of the gas output pressure/flow and the breathing measurement pressure/flow sensor sensors found in prior art oxygen conserving devices and ventilators. Further, this also allows for the use of much more sensitive pressure sensors for detecting breathing. In other mechanical ventilators, single lumen tubes are used and, as such, the flow output and breath "triggering" or detection are done in the same airline. Further, in other mechanical ventilators, only inhalation is detected. In other mechanical ventilators, exhalation and inhalation berating flows are spearhead using one-way check valves which comprise the dual limb ventilator circuit. In the mechanical ventilators (e.g., ventilator 500) of the present disclosure, the proximal pressure line is bidirectional (i.e., there are no check valves) and, as such, there is no pressure or flow "triggers" but rather pattern in breathing are mathematically computed based on nasopharynx pressure and/or breath detection sensor waveforms. In experimental use, by positioning the pressure sensors for breath detection in a separate lumen from the lumen used for gas output, it was found six times (6×) more sensitive pressure sensors can be utilized with a dual lumen setup for detecting breathing compared to single lumen pressure sensor. The ventilator 500 may also have rest, exercise, and/or sleep settings.

The flow rate of this continuous gas output to the patient (i.e., the output gas OG) is measured using a flow sensor 518. This flow sensor 518 may comprise a plurality of sensor methodologies. For example, the flow sensor 518 may utilize the thermo-transfer principle, also known as the calorimetric principle, to measure large ranges of gas flow rates when the gain factor of the flow sensor 518 is specifically calibrated and tested, such that the sensor output is amplified and two point trimmed at zero flow as well as a secondary flow rate point to optimize linearity within a certain flow rate range, such as 0-40 standard liter per minute (SLPM) gas flow. Under this thermo-transfer principle, inside the flow sensor module 518, a temperature sensor (not shown) is heated periodically by a heater element (not shown). The flowing gas absorbs heat energy and conducts it away. The resulting temperature change is an indication of flow, which translates to an analog voltage value that is then correlated to a flow output curve based on experimental data from the original equipment manufacturer (OEM) or sensor manufacturer during calibration and/or testing. Generally, this flow sensor 518 is a flow-through type sensor, wherein the flow sensor 518 includes a barb fitting inlet that connects to the oxygen or compressed air tubing 503, as well as a barb outlet to the flow outlet airline 520 with minimal resistance of fluidic loss. This flow outlet airline 520 can connect to a 22 mm breathing tube, hose barb, adapter, or other tubing connection thereafter. Further, this flow outlet airline 520 may also be fluidly coupled to an air entrainment device 522 described above in FIGS. 1-4. The flow sensor 518 can alternatively be other types of sensors, such as: turbine-type flow meters, rotometers, and membrane based differential pressure and temperature sensors that can be used to calculate flow rates, which can work especially well for laminar type or large volume/low pressure flows. the flow outlet airline 520 includes an airline outlet 521.

In certain embodiments, while using the oxygen or air tank 516, a bolus or partial bolus of oxygen or compressed air can be output to the patient at the beginning of their inspiration or end of their expiration. The peak inspiratory flow demands are the highest, potentially maximizing effective gas exchange in the lungs. This flow rate output from an air or oxygen tank 516 is not directly controlled, but rather is determined based on the orifice size/flow restriction of the solenoid valve 502 at a certain pressure. For example, with a 10 PSIG pressure gas source in the air or oxygen tank 516, the output flow rate through a 0.009 inch diameter orifice electronically controlled solenoid valve 502 in a completely open state would be 30 liters per minute (LPM), and with a 50 PSIG pressure gas source in the air or oxygen tank 516, the flow rate output would be 100 LPM. After the bolus volume, for example 50 mL at a flow rate of 30 LPM, from the air or oxygen tank 516 is outputted to user through the flow outlet airline 520, a continuous flow of input gas IG from the input gas source, for example 2 LPM, until the end of the useful phase of respiration such as 70% inhalation time, may follow. Then, the electronically controlled solenoid valve 502 closes.

During operation, user spontaneous breathing is detected using a separated breath detection airline 524 and an ultra-sensitive pressure sensor 526 for measuring breathing pressures (e.g., nasopharynx pressure). The breath detection airline 524 includes airline inlet 525. The airline inlet 525 is separated from the airline outlet 521 of the flow outlet airline 520 to minimize interference and therefore increase the accuracy of the pressure sensor 526. The pressure sensor 526 is in fluid communication with the breath detection airline 524. This breath detection airline 524 is configured to be connected to a 22 mm breathing tube, hose barb, adapter, or other tubing connection. The breath detection airline 524 is not in fluid communication with the flow outlet airline 520. By fluidly separating the breath detection airline 524 from the flow outlet airline 520, nasopharynx pressures can be measured without signal interference from the pressure/flow output from the ventilator 500, which would otherwise saturate the ultra-sensitive pressure sensor 526 required to measure nasopharynx pressures. In other ventilators and oxygen concentrators, a single airline is generally utilized in which a flow or pressure trigger threshold, ex. −0.13 cm $H_2O$ pressure, is used to determine the start of inhalation. This generally creates substantial lag in the ventilator gas output or false breathing triggers. Further, this necessitates the use of far less sensitive pressure sensors to prevent the pressure sensor from getting saturated from the output flow gas from the ventilator. Also, if flow is triggered based on a flow ramp, there can still exist substantial signal interference using a single airline.

In the presently disclosed ventilator 500, a breath detection software is used to predict transitions in breathing states and breathing time states, for example: transition from inhale to exhale, 70% inhalation time, transition from exhale to inhale, predicted PEEP based on % of exhalation. This breath detection software functions by measuring nasopharynx pressures using a separated breath detection airline 524, then storing the voltage values from the pressure sensor 526 in the controller 504 (e.g., microcontroller) RAM or EEPROM. For this reason, the controller 504 is in electronic communication with the pressure sensor 526. Breath transition states and timing predictions are detected through one or more mathematical calculations involving the pressure sensor voltage data including but not limited to: data filtering, differentiation, integration, linear regression analysis and linearizations, moving average calculations, Taylor series approximations, steady state error compensation, model predictive control, proportional control, fuzzy control theory, ODEs, radial basis functions, quadratic-program approximation, feedforward control, adaptive control, PI and/or PID control, SISO control schema, and Laplace transformations. A moving average calculation may be used such that, if the filtered pressure sensor data falls below the moving average, a transition from an inhale to an exhale is predicted.

Other sensors can also be used independently, in combination with, or to replace the pressure sensor(s) 526 described herein to measure data trends in breathing, implement predictive breath detection software algorithms, and/or actuate at certain threshold values and/or ramps including but not limited to: flow sensors, CO2 gas concentration sensors, O2 gas concentration sensors, temperature sensors, humidity sensors, volume sensors, and/or acoustic sensors. This breath detection is used to determine when to output ventilator gas, which can include compressed air, oxygen, or a mixture thereof, to the patient at the correct time in order to provide pressure/ventilatory support, as well as facilitate effective lung gas exchange, ventilation, and manage arterial blood gases (ABGs) such as $PaCO_2$ and $PaO_2$. Accordingly, the pressure sensor 526 is configured to generate sensor data indicative of breathing by the user, and the controller 504 is programmed to detect the breathing of the user based on the sensor data received from the pressure sensor 526.

The components and electromechanical subassemblies of the ventilator 500 are contained within an electronics enclosure 528, which can be manufactured using a plurality of manufacturing methods including but not limited to: injection molding, 3D printing, CNC machining, sheet metal fabrication, PCBA, wire harnessing, and other manual or automated manufacturing techniques not described herein.

Figure 6:
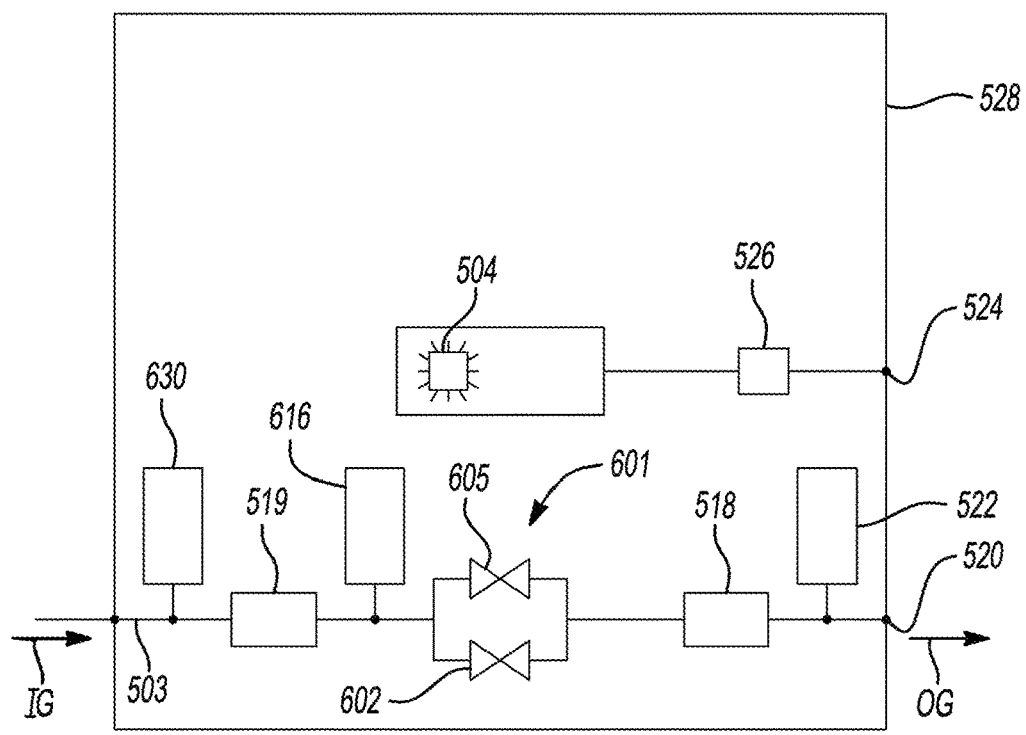
FIG. 6 is a schematic illustration of a ventilator with proportional control valves and an air volume tank to modulate high pressure or low pressure oxygen or compressed air source, wherein the ventilator is configured to detect a high pressure or low pressure oxygen source from a single input airline using two proportional control valves and modulate the output gas.

With reference to FIG. 6, a ventilator 600 includes one or more electronically controlled proportional control valves 602, 605 and an air volume tank(s) 616. The ventilator 600 is similar to the ventilator 500, except for the features described below. These proportional control valves 602, 605 and air volume tanks 616 can be configured in numerous ways for different purposes. The proportional control valves 602, 605 are part of a valve arrangement 601 and can be fluidly coupled in parallel. One or more proportional valves 602, 605 may be used to output a high pressure or low pressure oxygen/compressed output gas OG. Further, the ventilator 600 can detect a high pressure or low pressure oxygen source from a single input airline (i.e., tubing 503) using a high pressure proportional control valve 605 and a low pressure proportional control valve 602 to modulate output gas OG. To do so, the ventilator 600 may include an input pressure sensor 630 to detect input gas source pressure (i.e., the pressure of the input gas IG), or by utilizing one proportional valve 602 or 605 in the fully open position for a short time period, such as 50 milliseconds, to determine the flow rate output detected by the flow sensor 518. The flow rate can be used to calculate the pressure of the input gas IG based on the orifice diameter/flow restriction of the electronically controlled proportional control valves 602, 605.

When the proportional control valve(s) 602, 605, are closed, the input gas IG of continuous flow can accumulate in the air volume tank 616. This can serve the following purposes: bolus output at the beginning of the useful phase of respiration, a method of conserving oxygen/compressed air, and/or a method for proportional flow control of the gas output, such that a high output flow rate (e.g., 200 LPM) can be outputted from a low input flow rate (e.g., 6 LPM). Depending on the application, the size/volume specifications of the air volume tank 616 will be different. For example, if oxygen conservation (e.g., when oxygen accumulates when the patient is exhaling) is the primary focus, a much larger air volume tank 616 should be sized and used in conjunction with proportional flow control. However, if the goal is just to output a bolus of oxygen at the beginning of inspiration or end of expiration during each breath with no proportional flow control, a much smaller air volume tank 616 should be sized, which can further enhance portability of the device but reduce oxygen conservation or high flow output capabilities. The use of proportional flow control is especially relevant for 50 PSIG high pressure gas sources, such as medical hospital oxygen wall supplies, where a large bolus of high-pressure gas can cause over-inflating of the lungs or barotrauma.

In addition to the flow sensor 518, the ventilator 600 may include a second flow sensor 519. Accordingly, the flow sensor 518 may be referred to as the first flow sensor or output flow sensor, and the second flow sensor 519 may be referred to as the input flow sensor. As such, the flow of the input gas IG may be measured using the second flow sensor 519. The controller 504 may be programmed to maintain the input gas IG flow at a fixed oxygen conservation ratio (e.g., 3×), and the input gas IG may be accumulated in the air volume tank 616 when the proportional control valves 602, 605 are closed. The flow of the input gas IG may be, for example, 2 LPM. Hence, a 6 LPM flow of gas would be outputted from the air volume tank 616, and one or more of the proportional control valves 602, 605 would be open during the useful phase of respiration. This proportional flow control can utilize PI or PID control algorithms. The proportional gain Kp and integrator values of the PI or PID control algorithms may be, for example, experimentally determined and set by the manufacturer to have the smoothest and most accurate flow rate outputs at a given range. The proportional gain Kp and integrator values of the PI control may be automatically updated by the controller 504 based on different input flow conditions detected by a second flow sensor 519 as well as actual output flow detected by first flow sensor 518 vs predetermined output flow rates. The controller 504 may use feedback or feedforward control to compensate for error and maximize flow rate precision. The flow of the output gas OG to the user may be time controlled. For example, the duration of the flow of the output gas may be set to be a variable time, thereby supplying the output gas OG with variable volume/pressure profile based on user breathing times (e.g., 90% exhale time for start of flow and 70% of inhale time for end of flow). Alternatively, the output gas OG supplied to the user may be volume controlled, pressure controlled, flow controlled, or a combination therein. Further, the output gas OG does not necessarily need to be a square waveform, but rather can consist of different flow, pressure, and/or waveform patterns, which can be dynamically adjusted by the ventilator 600 on a breath by breath basis. Some of these waveform patterns can include descending ramp, sinusoidal, oscillatory, step functions, and/or a combination of waveforms thereof, which can also be generated using mathematical patterns based on sensor data and lung models programmed into the controller 504.

In this configuration, the oxygen conservation ratio is a fixed value. Alternatively, the flow rate of the output gas OG may be controlled by the user. In one example, the user can have a flow dial or knob that specifies a flow rate of the output gas OG of 4 LPM. As such, the oxygen conservation ratio would be algorithmically adjusted by a software program being run by the controller 504 based on the user input. This adjustment in output flow rate can be performed by the ventilator 600 based on computations involving one or more sensors (e.g., the pressure sensor 526 or external sensors or devices not contained in the ventilator 600). Sensors or devices that can be used to automatically adjust oxygen flow rate to the user include, but are not limited to, sensors or devices that measure the following, independently or in combination thereof: breathing flows, pressures, $O_2$ concentrations, $CO_2$ concentrations, humidity, acoustics/voice, temperature, trace gas or liquid concentrations, pulse oximetry, vital signs such as heart rate and/or blood pressure, and/or physical movement of the ventilator 600.

The ventilator 600 may include proportional pressure control valves instead of proportional flow control valves 602, 605. This would be especially useful for pressure-controlled ventilators, as well as low pressure (i.e., less than 5 PSIG) input gas sources where the springs inside existing miniature electronically controlled proportional control valve designs are generally too stiff to precisely control the flow of low pressure gas. These pressure control valves generally function as closed-loop electronic air pressure regulators. Single and double loop pressure control valve architectures generally include two or more valves, a manifold, internal pressure transducer, and electronic controls (not shown). Output pressure is proportional to an electrical signal input. Pressure is controlled by two solenoid valves. One valve functions as the inlet control and the other as an exhaust. The pressure output is measured by a pressure transducer internal to the proportional pressure control valve system and provides a feedback signal to the electronic controls. This feedback signal is compared against the command signal input. A difference between the two signals causes one of the solenoid valves to open allowing flow in or out of the system. Accurate pressure is maintained by controlling these two valves. By controlled pressure, the flow is slowed down and hence a maximum flow rate from the air volume tank 616 can be set that is lower than the flow rate that would be output from an air volume tank 616 and standard electronically controlled solenoid valve 502 (FIG. 5) that fully opens. With this proportional pressure control, the pressure output can be precisely controlled to reduce the risks of barotrauma or lung overinflation from the ventilator gas output. Flow control can also be executed indirectly by controlling pressure by measuring flow rates using the first flow sensor 518. The flow may be controlled, for example, by varying the times of the inlet control and exhaust timings of the valves in the proportional pressure control system.

Figure 7A:
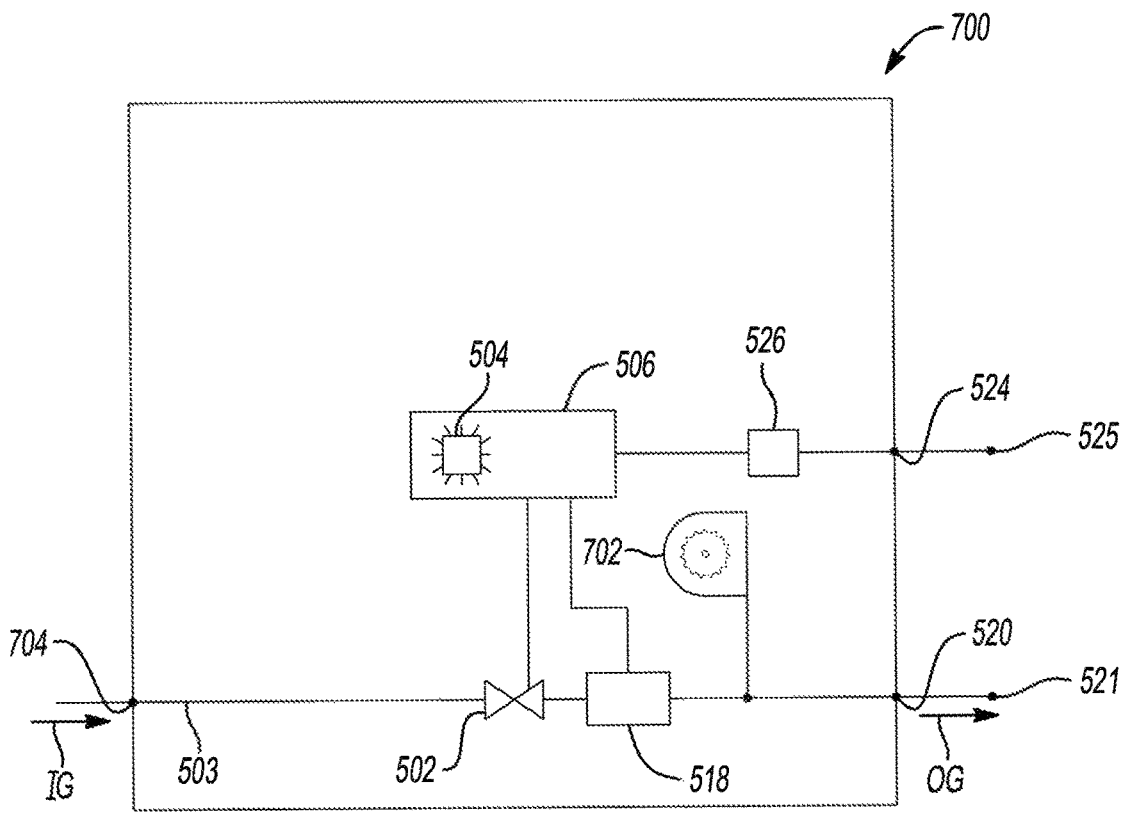
FIG. 7A is a schematic illustration of a ventilator that uses an ultra-low pressure gas source, and a turbine blower configured to add energy to increase the pressure of the gas.

With reference to FIG. 7A, a ventilator 700 uses one or more ultra-low pressure gas sources. The structure and operation of the ventilator 700 is substantially similar to the structure and operation of the ventilator 500 (FIG. 5) described above, except for the features described below. The ventilator 700 includes a turbine or pressurization pump 702 in fluid communication with the tubing 503. The turbine 702 adds energy to increase pressure of the output gas OG, thereby allowing the flow restrictions to be minimized. Accordingly, the ventilator 700 can use smaller tubing patient interfaces (e.g., flow outlet airline 520 and breath detection airline 524). In other CPAP devices and ventilators, large bore breathing tubing (e.g., 22 mm diameter tubing) is used due to the low pressure gas output, which generally ranges from 4-20 cm $H_2O$ pressure. In some cases, this air entrainment ratio can exceed 25 times the amount of volume/flow rate of the input gas flow IG. Oxygen concentrators or generation devices may be used to generate ultra-low oxygen output pressures in order to minimize the energy consumption of the gas separation process. Assuming 2 LPM oxygen gas is produced at 0.6 PSIG output pressure and 49 LPM of air entrainment, this would result in a total pressure for the air-$O_2$ mixture of 0.024 PSIG. Based on flow coefficient calculations, this would mean only 32.35 LPM of gas with a 0.024 PSI pressure differential can flow through a 10 mm circular patient interface orifice. Hence, if a discreet and small bore tubing were to be used as the patient interface, for example with a dual lumen nasal cannula or oxygen eyeglass frames with nasal pillows, either lower amounts of air entrainment or higher pressure oxygen gas would be required for the patient interface to be feasible. Hence, in the ventilator 700, the turbine or pressurization pump 702 is used to increase the pressure of the input gas IG in the oxygen from an oxygen concentrator (not shown) or gas source from an inlet 704 that is in fluid communication with the ventilator tubing 503. The valve 502 is in fluid communication with the ventilator tubing 503. The input gas flowing from inlet 704 flows through a valve 502 (e.g., a solenoid valve) and is measured by the flow sensor 518. The input gas IG from inlet 704 flows through the air entrainment device 518, and then flows to the turbine or pressurization pump 702. Hence, the pressure of the air-$O_2$ mixture is increased by adding energy into the ventilator 700. For example, if the pressure of the air-$O_2$ gas mixture increases from 0.024 PSIG to 0.146 PSIG, then 19.7 LPM of gas can flow through ventilator tubing 503 with a 2.4 $mm^2$ orifice cross sectional area. This would make, for example, a pair of discreet oxygen eyeglasses that utilizes two separate 1.2 mm diameter by 2 mm oval air channels feasible with 40 LPM of flow through the patient circuit.

Figure 7B:
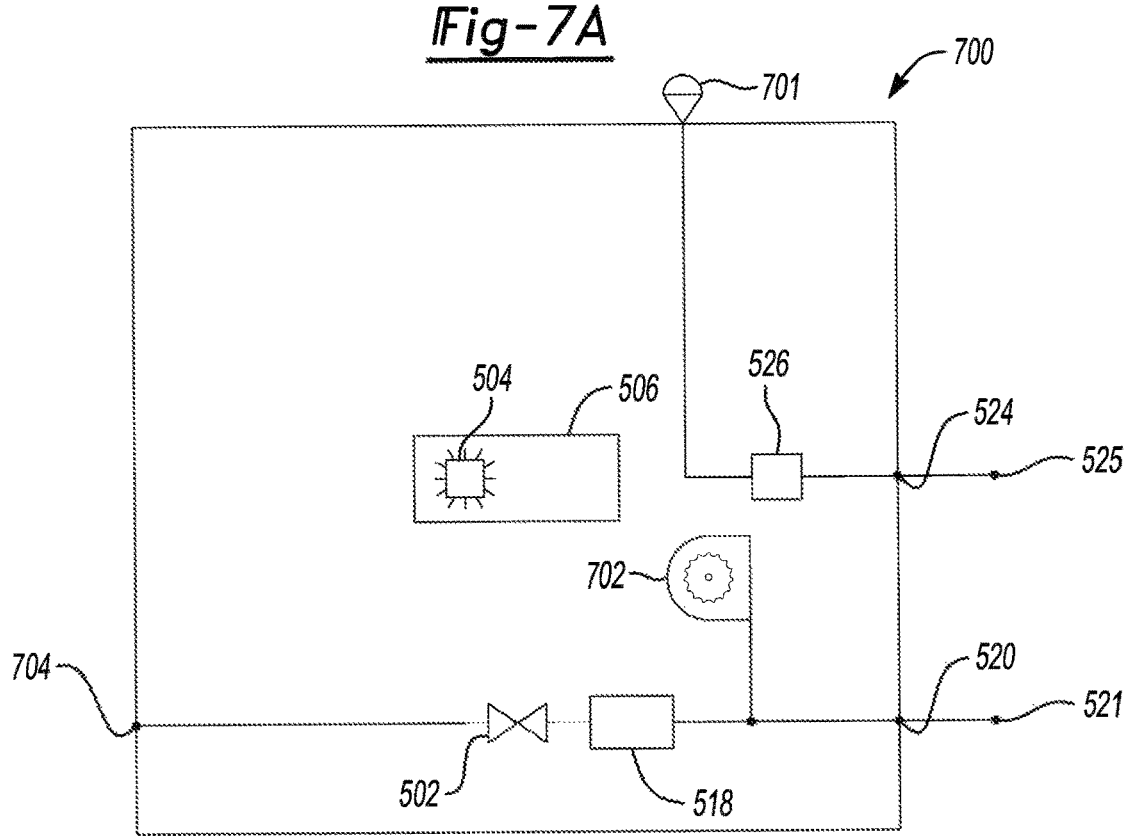
FIG. 7B is a schematic illustration of a ventilator that uses a positive end-expiratory pressure (PEEP) valve.

In some embodiments as shown in FIG. 7B, the ventilator 700 may include a PEEP valve 701, such as a mechanical or pneumatic valve. The PEEP valve 701 is in fluid communication with the breath detection airline 524.

Figure 7C:
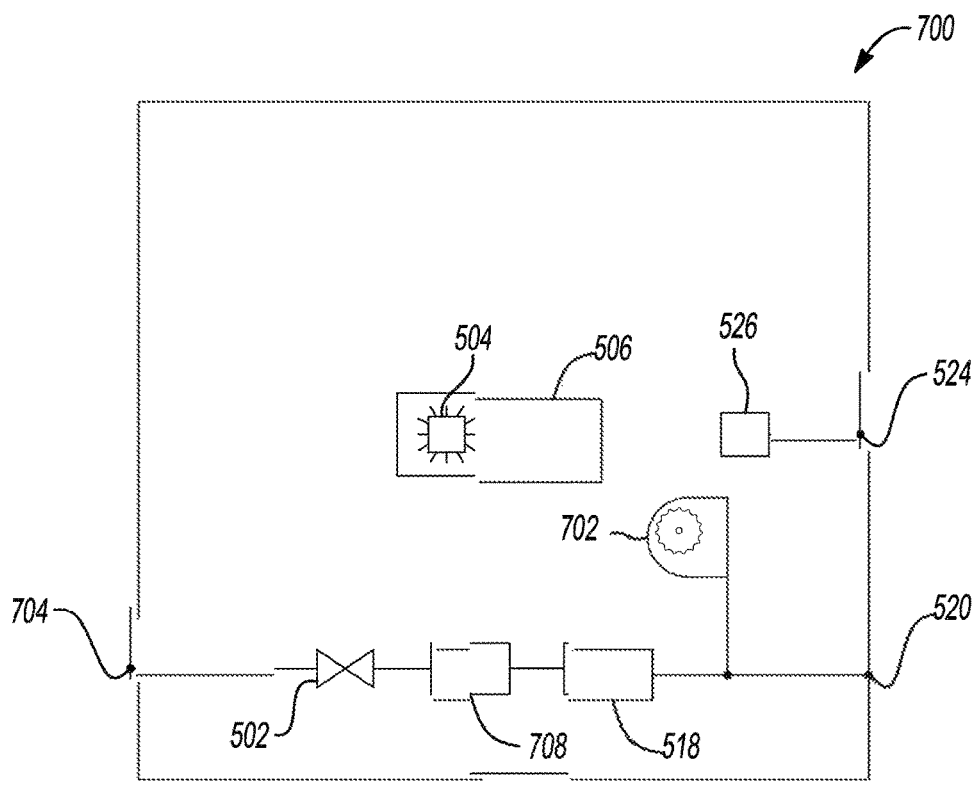
FIG. 7C is a schematic illustration of a ventilator that uses an oxygen concentrator.

In some embodiments as shown in FIG. 7C, the ventilator 700 may include an internal oxygen concentrator 708, which can be fluidly connected to allow external gas sources. This internal oxygen concentrator 708 can be of several types, such as, but not limited to: pressure swing adsorption, vacuum pressure swing adsorption, ultra-rapid pressure swing adsorption, oscillator pressure swing adsorption, "molecular gate" pressure swing adsorption, thermally cycled pressure swing adsorption, thermal swing adsorption, Joule-Thomson liquefaction units for the production of liquid oxygen from atmospheric air, gaseous oxygen tanks, liquid oxygen tanks, membrane based gas separation units, and combinations thereof.

Figure 8A:
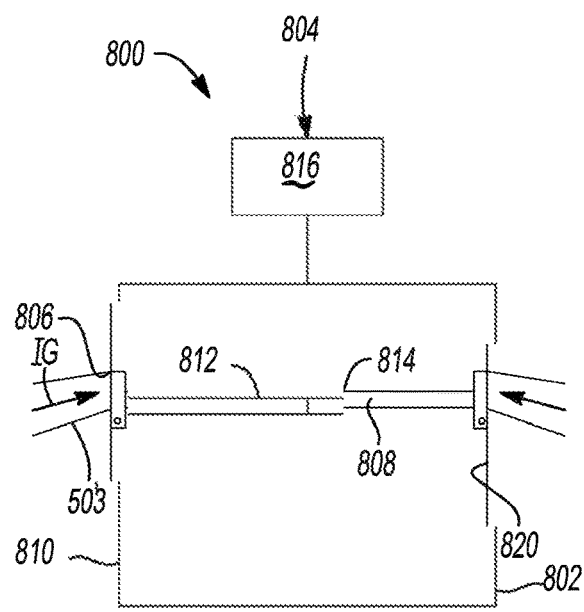
FIG. 8A is a schematic cross-sectional view of an electronically controlled check valve using pressure actuators, wherein the electronically controlled check valve is shown in an OFF state.
Figure 8B:
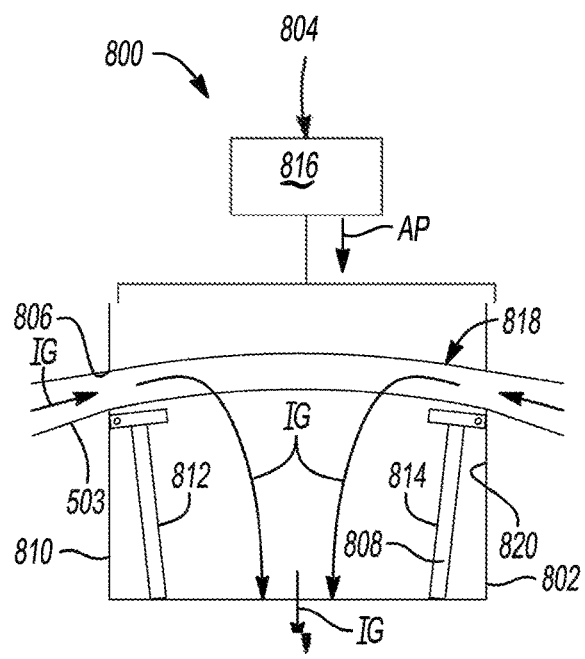
FIG. 8B is schematic cross-sectional view of the electronically controlled check valve of FIG. 8A shown in an ON state.
Figure 9A:
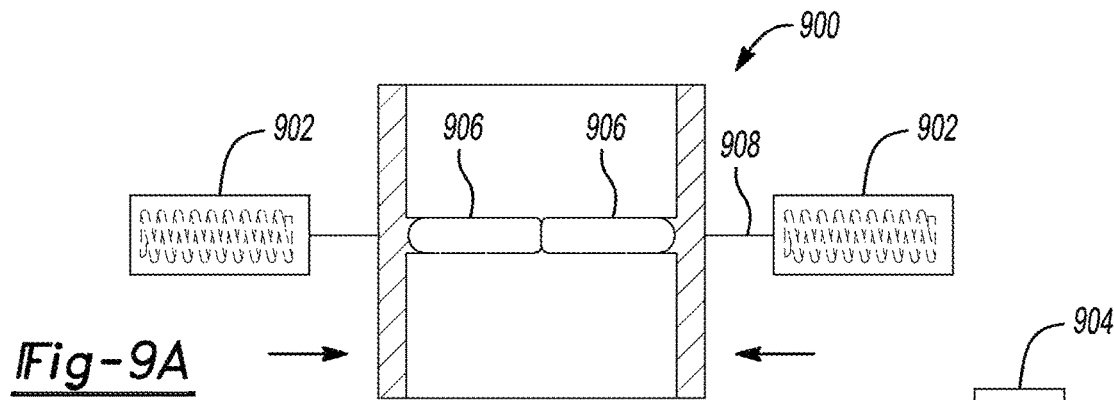
FIG. 9A is a schematic cross-sectional view of an electronically controlled check valve using electromagnetic actuators, where the check valve is in a closed state.

With reference to FIGS. 8A and 8B, a check valve actuation system 800 for ventilatory output using ultra-low-pressure gas sources is described. For example, a low-pressure input oxygen or compressed air gas flow of 6 LPM may be used with exemplary gas source pressures of 0.2 PSIG±0.05 PSIG. A check valve 802 with 0.3 PSIG cracking pressure and 0.25-inch diameter may be selected. A pressure actuator 804 can be used to open the check valve 802 initially by creating a minimum flow (e.g., 0.1 LPM) required to actuate the check valve 802 at the cracking pressure of 0.3 PSIG. The check valve 802 is configured to then be kept open during the period of useful respiration through a plurality of methods. For example, the check valve 802 is mounted in a vertical position such that only a pressure actuator 804 can open the check valve 802. The end of the check valve 802 is capped and then the input gas IG can flow horizontally through a valve inlet 806 and then through an open check valve flap 808. The flap 808 includes a first flap portion 812 and a second flap portion 814. The check valve 802 includes a sidewall 810, and the valve inlet 806 extends through the sidewall 810. Each of the first flap portion 812 and the second flap portion 814 is pivotally connected to the sidewall 810, thereby allowing the flap 808 to move between a closed state (FIG. 8A) to an open state (FIG. 8B). The open check valve flap 808 may be thick (e.g., 0.2 inches) but it has low resistance/low cracking pressures to allow easy opening by the pressure actuator 804. The pressure actuator 804 is configured to actuate the check valve 802. The check valve 802 is in a vertical orientation. Upon actuation of the pressure actuator 804, the check valve 802 switches from an OFF or closed state to an ON or open state. Specifically, upon actuation of the pressure actuator 804, a downward actuating pressure AP is exerted on the flap 808, causing the flap 808 to move from the closed state to the open state. When the check valve 802 is in the ON or open state, the input gas IG can flow through the flap 808 from the tubing 503 and then curve downward through a tube that connects to the outlet of the check valve 802.

The pressure actuator 804 may include metal or rubber bellows, air cylinders, pneumatic pistons, servo motors, electromagnetic coils, oscillators, hydraulic actuators, air volume tanks, turbines, air blowers, and other fluid power mechanisms to pressurize a volume of gas at low or high frequency, or actuate the check valve 802. The pressure actuator 804 may include a piezoelectric micro-blower 816 that utilizes a high frequency piezoelectric oscillator that vibrates at 28 kHz frequency such that a mean effective pressure (MEP) is created. This generated MEP may be in the form of an oscillatory pressure waveform. The latency of the mechanical response of the check valve 802 to pressure changes would be slower than the electrical response of the piezoelectric oscillators. This generated MEP may be electronically controlled by turning the micro-blower 816 ON or OFF. For example, a MOSFET switch (not shown) may be used to turn the micro-blower 816 ON or OFF to increase pressure in the small chamber/volume (in the check valve 802) by the user or machine. The air accumulates at the valve inlet 806 of the check valve 802 just enough to exceed the cracking pressure of the check valve 802 during the useful phase of respiration, while also minimizing energy consumption of the piezoelectric micro-blower 816.

When the check valve 802 is in the closed state, the edges of the first flap portion 812 prevent the flow of inlet gas IG through the check valve 802, reducing the amount of volume that needs to be pressurized to actuate the check valve 802 using the pressure actuator 804. The check valve 802 also has an air channel 818 defined on an inner valve surface 820 of the check valve 802. The air channel 818 can be a ring-shaped and can therefore extend along the entire circumference of the inner valve surface 820. Further, the air channel 818 has a convex shape. The air channel 818 is disposed around the first flap portion 812. When the check valve 802 is in the closed state. The first flap portion 812 covers the valve inlet 806, thereby preventing the inlet gas IG from entering the check valve 802 through the valve inlet 806. When the check valve 802 is in the open state, the first flap portion 812 no longer covers the valve inlet 806 and therefore the valve inlet 806 is open. As a consequence, the inlet gas IG can flow from the ventilator tubing 503 to the check valve 802 through the valve inlet 806. Then, due to the convex shape of the air channel 818 the inlet gas IG, a convex gas flow profile is created along the air channel 818. As such, the inlet gas IG is outputted through the check valve 802 in an unrestricted flow pattern via the valve inlet 806. The thickness of the first flap portion 812 is equal to or greater than the diameter of the valve inlet 806, allowing the first flap portion 812 to block the valve inlet 806 when the check valve 802 is in the closed state.

The check valve 802 can be in a horizontal-flow-through orientation. Consequently, the pressure actuator 804 can increase the pressure in a small section of the ventilator tubing 503 right before the check valve 802 to, for example, 0.3 PSIG. In such a case, adding energy to increase the pressure inside the ventilator tubing 503 may be beneficial to move the inlet gas IG to exceed the cracking pressure of the check valve 802. Using ideal gas state equations such as AE=RT[(P0/P1)−1+ln(P1/P0)], and then translating the flow rate into volume and then mass using known densities for air at certain temperatures, it can be calculated that 10 Wh of power consumption would, causing the check valve actuation system 800 to continuously increase the pressure of the inlet gas IG by 0.1 PSIG. The power consumption may be reduced if the variance in pressures from the inlet gas IG is significantly smaller.

The check valve 802 may be electronically controlled to have variable cracking pressures. To do so, a notch, for example, may be embedded in the edge of the flap 808. A heating element may be used. By heating the flap 808, the edge of the first flap portion 812 expands and is locked in by the notch (not shown), closing the check valve 802. The heating would depend on the coefficient of thermal expansion of the material of the first flap portion 812.

With reference to FIGS. 9A, 9B, 9C, 10A, 10B, 10C, and 10D, an electronically controlled check valve 900 that utilizes an electromagnetic actuator 902 is described. These can include piezoelectric actuators, electromagnetic coils, linear motors, and servo motors. Other types of actuators can also be utilized. Some electronically controlled solenoid valves have small orifice sizes due to the fact that generally a shaft or pin needs to be accelerated by an electromagnetic coil, which creates limitations and tradeoffs related to power consumption, response times, and orifice diameter. For example, a 0.5-inch diameter orifice electromagnetic solenoid valve would require a large coil and high-power consumption to accelerate the shaft or pin such that response times are <100 milliseconds. Some passive check valves do not consume any power and have large orifices, such as 0.5 inch in small form factors, and cannot be electronically controlled. The electronically controlled check valve 900 seeks to solve these problems. The electronically controlled check valve 900 includes a latch 904 and an electromagnetic actuator 902, such that a large orifice can be opened, for example >50%, while only having to accelerate an electromagnetic coil/shaft a distance of <25% the length of the orifice diameter. These numbers are only examples.

The check valve 900 includes one or more of the following: a check valve flap(s) 906, electromagnetic actuator(s) 902, and latch(s) 904. The actuator 902 operates by linearly accelerating a pin or shaft 908 using electromagnetic forces from a coil through a latch 904 with a particular cutout pattern with tolerances such that the pin or shaft 908 will easily slide through. This pin or shaft 908 is generally circular in shape and is machined to include two rectangular notches that exceed the outer diameter of the shaft 908. Once the pin or shaft 908 enters the latch 904 in the proper position, such as after the backplate, the electromagnetic actuator 902 rotates the pin or shaft 908 a quarter turn or 90 degrees to lock the check valve flap 906 in place in the closed position due to the mechanical properties of the latch 908, similar to turning a key. This turning mechanism can be controlled using a separate or integrated servo motor or rotary actuator (not shown), wherein the rotational position of the actuator can be measured and controlled, using a hall effect sensor or other means of sensing. This latch 904 can be placed in a variety of positions below or above the inlet of the check valve flap 906, including but not limited to: near the center, near the edge of the flap, straight down, straight up, slanted at a positive 57 degree angle, slanted at a negative 80 degree angle, slanted at a positive 15 degree angle. This should be mechanically designed in such a way that the travel distance of the actuator shaft 908 is minimized. The electromagnetic actuator 902 may be a rotary actuator and may include components, which may be micro or nanofabricated and/or machined, including but not limited to: electrostatic actuators, thermal actuators, electromagnetic rotors, and fluidic actuators. For example, a solenoid armature can be designed such that the armature can be rotated back and forth in a linear or non-linear pattern at high cyclical frequency such that its position can be precisely controlled, similar to the actuator and head mechanism found in hard disk drives or HDDs. Consequently, the latch 904 can be easily and quickly released and/or held in place at a cyclical rate, and/or various durations of time. It is contemplated that the electromagnetic actuator 902 may include a guide screw (not shown). As such, the electromagnetic actuator rotates the pin or shaft 908 linearly across a guide screw at a precise position at high linear speed using fast rotational speeds. The rotational position of the pin 908 can be measured using a hall effect sensor or other means of sensing such as force or position when lightly contacting the face of the latch 904. The direction of rotation of the electromagnetic actuator 902 can be reversed such that the pin or shaft 908 can be moved back and forth using the guide screw. The pin 908 can be released from the latch 904 and rotate counterclockwise down the guide screw using the recoil force from a spring (not shown) that is actuated by rotating the pin 908 using the guide screw.

Figure 10D:
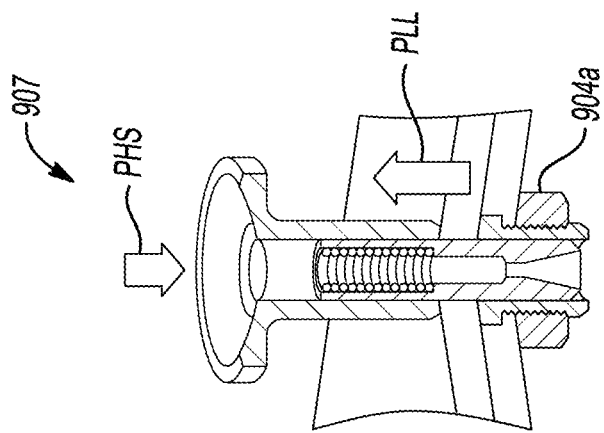
FIG. 10D is a schematic, cross-sectional perspective view of the actuator moving from the engaged position toward the disengaged position.
Figure 10C:
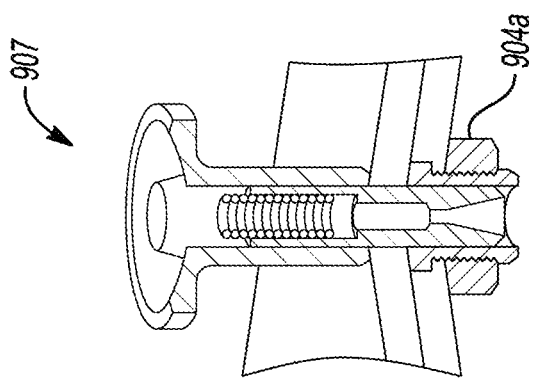
FIG. 10C is a schematic, cross-sectional perspective view of the actuator of FIG. 10A, wherein the actuator is in an engaged position.
Figure 10B:
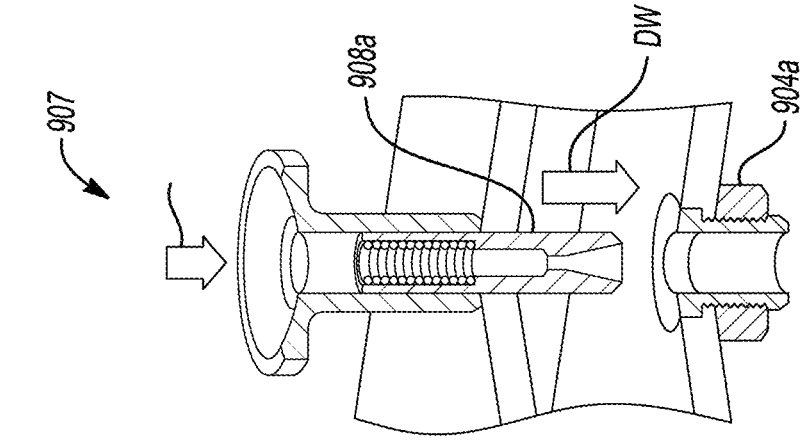
FIG. 10B is a schematic, cross-sectional perspective view of the actuator of FIG. 10A, wherein the actuator is a disengaged position.
Figure 10A:
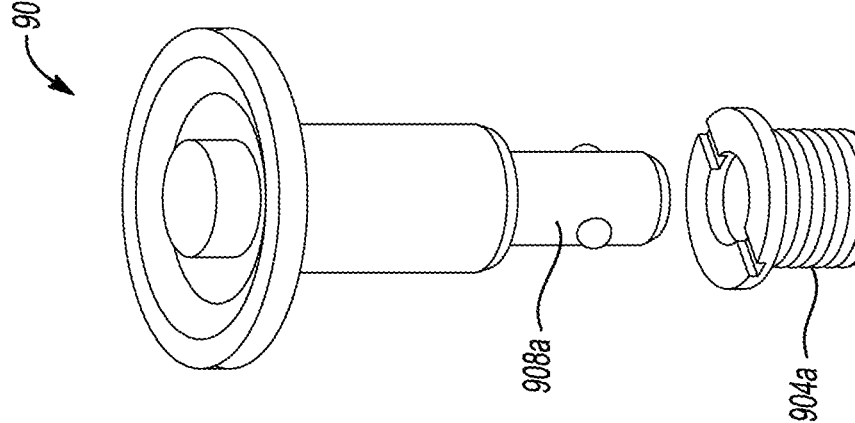
FIG. 10A is a schematic exploded view of an actuator for the electronically controlled valve of FIG. 9A.
Figure 12:
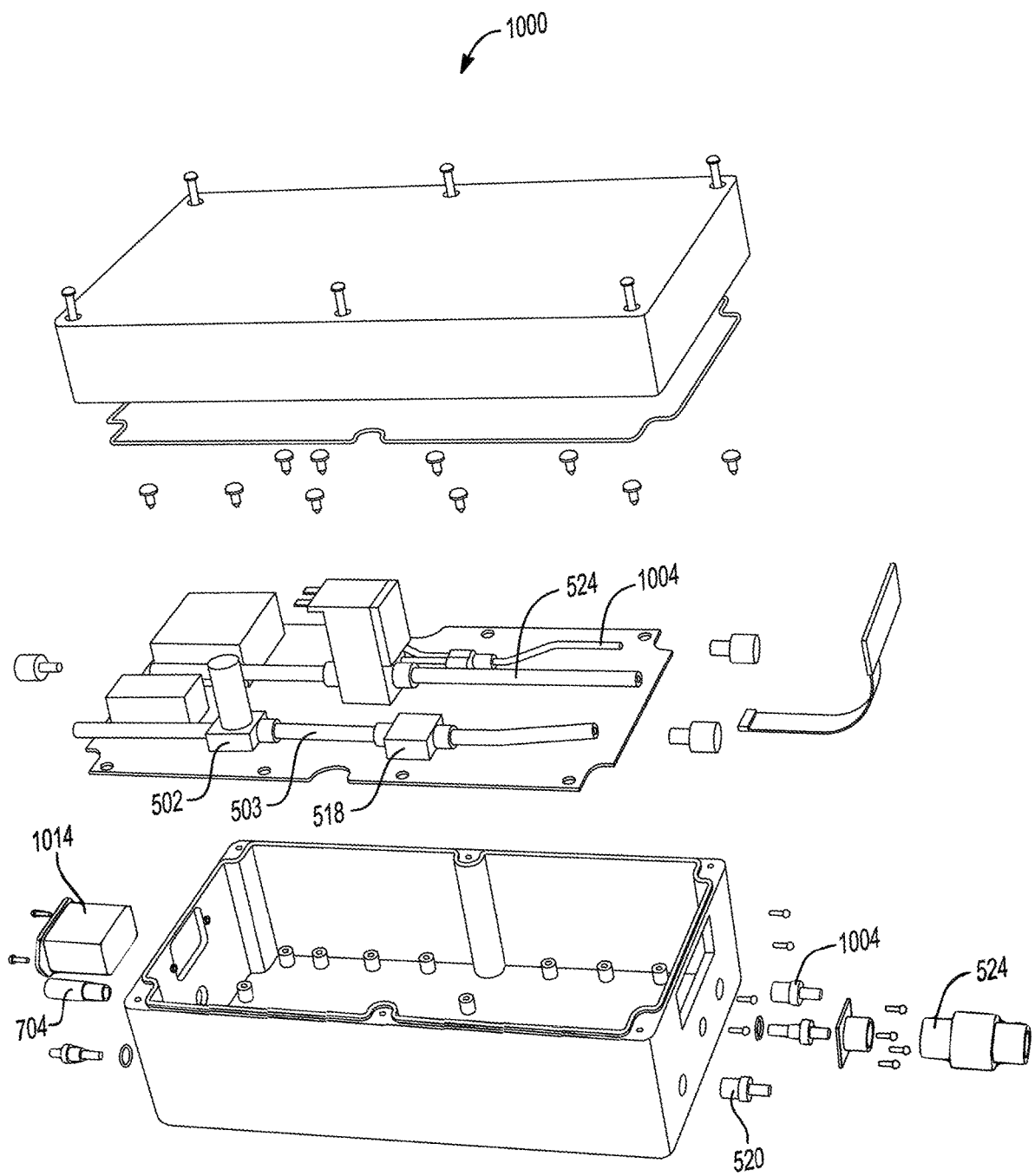
FIG. 12 is a schematic exploded, perspective view of the ventilator of FIG. 11.
Figure 13:
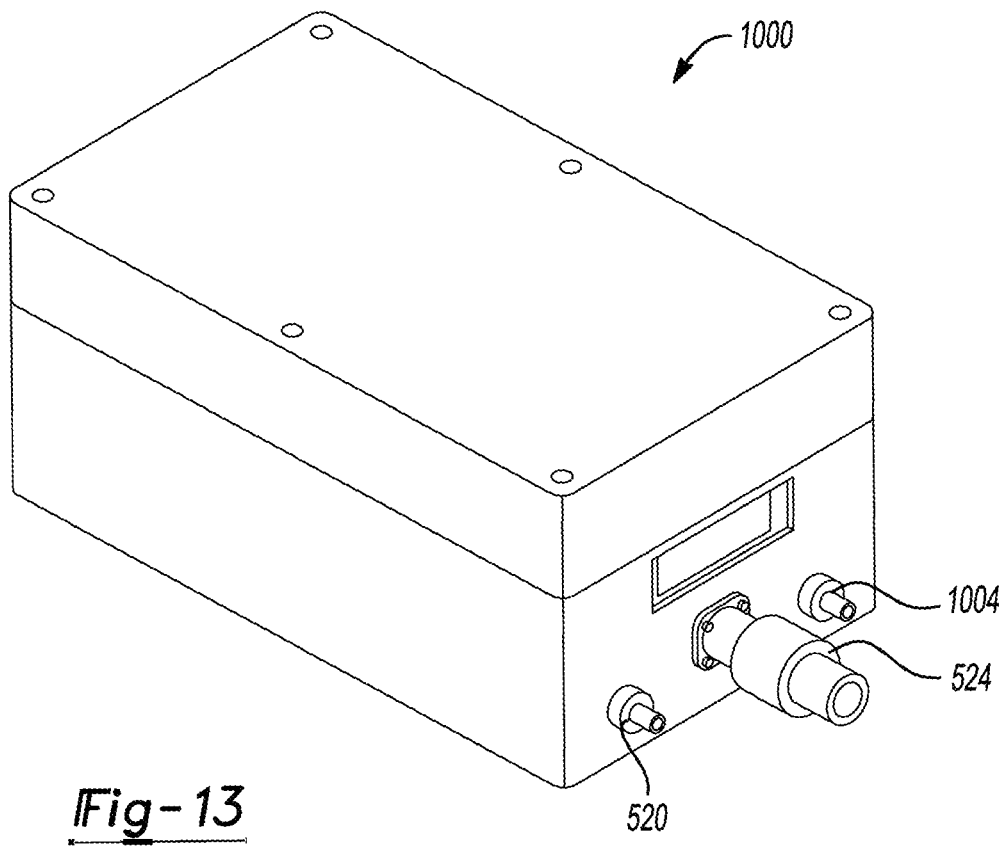
FIG. 13 is a schematic, perspective front view of the ventilator of FIG. 11.
Figure 14:
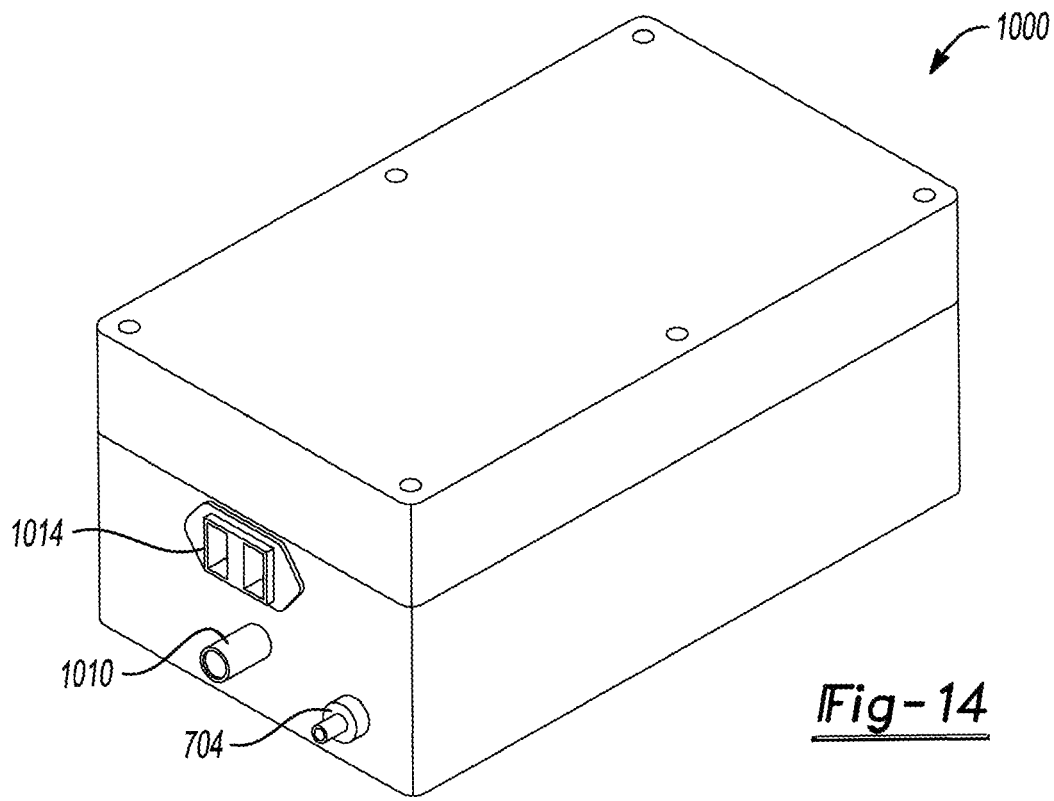
FIG. 14 is a schematic, perspective rear view of the ventilator of FIG. 11.

The pin 908 and the latch 904 may be configured as a "button locking" pin latch mechanism 907 as illustrated in FIGS. 10A, 10B, and 10C. In such a case, only a linear solenoid or actuator, and no rotary or combo rotary and linear motion actuator, is required. The actuator 902 exerts a linear force LF to accelerate a pin 908a into a latch 904a. As a result, the pin 908a moves in a downward direction DW into the latch mechanism and is clamped into place by the latch 904a. The actuator pin or shaft 908 may contain inside or have a spring (not shown) around the pin or shaft 908a. As such, when the electromagnetic actuator 902 (e.g., linear solenoid actuator) pushes (as is shown by arrow PHS) on the pin 908a after clamped into place by the latch 904a, the pin 908a would be pulled (in the direction PLL) by the recoil force of the spring. Only one actuator 902 may be required such that a mechanical latch 904 can hold both flaps 906 closed when the pin 908 is clamped into the latch 904. In one embodiment, one or more mechanical latch(s) 904 are proximal to the flaps 906, such that a portion or the entirety of the pin latch mechanism 907 is embedded or comprise the flaps 906, such that the distance of linear travel between the mechanical latch(s) 904 and the flaps 906 is minimized, for example less than 1 mm travel distance.

The electronically controlled valve 900 may not just be useful for ventilator or respiratory device applications, but also in applications such as industrial automation. For example, some high pressure compressed air systems can be replaced with lower pressure blower based compressed air systems to reduce energy consumption by >20% using electronically controlled check valve 900 with compact size profiles, low power requirements, and large orifice sizes.

With reference to FIGS. 11, 12, 13, and 14, a ventilator 1000 has invasive and non-invasive ventilation modes. The structure and operation of the ventilator 1000 is substantially similar to the ventilator 500, except for the features described below. The ventilator 1000 has a carbon dioxide ($CO_2$) exhalation valve 1002 inside the ventilator 1000. In some embodiments, the exhalation valve 1002 is not a component of the ventilator circuit. Further, in other embodiments, this exhalation valve 1002 could comprise a mechanical/pneumatic PEEP valve instead of an electronically controlled variant, wherein the PEEP provided to the patient could be manually adjusted by the patient by rotating the knob of the valve (not shown), which controls the spring force that creates a resistance to the patient's exhalation that once this resistance is overcome, the PEEP valve opens. In some embodiments, this PEEP valve is normally open wherein there is an electronically controlled bypass that opens if the main power supply is shut off while in use or fails, which could be powered using a miniature servo motor and the ventilator's backup battery (both not shown). This PEEP valve or exhalation valve 1002 could exist in non-invasive or invasive ventilators, as well as ventilator embodiments with one or more lumens. This ventilator 1000 can operate in a variety of ventilatory modalities including, but not limited to, one or more of the following: Assist Control, SIMV, Pressure Control Ventilation, Volume Control Ventilation, Volume Assist or Augmented Ventilation, Proportional Assist Ventilation, Bioimpedance controlled ventilation, High Frequency Ventilation, and/or Neutrally Adjusted Ventilatory Assist.

The Assist Control ventilation mode may be especially useful and/or optimized for acute respiratory distress syndrome (ARDS) and/or COVID-19 ventilator patients, and/or for patients with Stage III-IV chronic obstructive pulmonary disease (COPD). In the present disclosure, control breaths are defined as machine breath output over a fixed period of time. For example, a machine breath will be output every 6 seconds when patient spontaneous inspiration cannot be detected, and, hence, the patient is non-spontaneous breathing when control breaths are output since the ventilator 1000 is breathing for the person. The control breath settings are controllable by the user or machine, with tidal volume output controlled by the valve 502, and, in certain embodiments, a calculated fixed value based on input flow. Other settings that can be controlled include inhalation to exhalation ratios, for example. Each control tidal volume output can have the same or varying duration. Fixed tidal volume values can be programmed into the controller 504 as text based numeric values based on input flow rate of the input gas IG rounded to nearest 0.1 LPM for example. Assist breaths are defined as spontaneous breaths detected and triggered between control breaths using nasal pharynx pressure sensor breath detection software. $O_2$ or compressed air flow rate of the input gas IG is controlled by the user or machine between, for example 0-200 LPM, which is measured by the flow sensor 518. Gas sources include but are not limited to: blower airflow controller, wall oxygen supply in hospital, oxygen concentrator, and/or air compressor such that ventilator tidal volume setting adjustments are done either automatically by the machine using the firmware/software of the electronic board 506 or physically by the user using a knob, switch, touchscreen, and/or any other human-computer interface. A square waveform fixed tidal volume output can be generated at a preset volume based on $O_2$ flow rate input detected by the flow sensor 518. However, a descending ramp, ascending ramp, sinusoidal, and/or other or combinations of waveforms thereof can be generated by the ventilator 1000 as the tidal volume output. Assist breath tidal volume can be the same or different compared to control breath tidal volume. With auto volume control, the ventilator tidal volume output may be a fixed value based on input compressed air or $O_2$ flow that begins being output at for example 90% exhale time to provide low level PEEP or during start of inhalation to provide IPAP.

A low tidal volume low peak inspiratory flow (PIF) ventilation may be used as a lung protective strategy for ARDS. While other PIFs of 180 LPM can generate high peak inspiratory pressures and cause barotrauma in certain ventilated patient populations, the ventilator 1000 generates between 150 mL to 750 mL tidal volumes. However, ventilators with higher or lower tidal volume output settings can be created. An inspiratory hold time is created by closing both the $CO_2$ exhalation valve 1002 and the tidal volume output valve 502 to generate a plateau pressure that can be measured and improve oxygenation/gas exchange in lungs, which generally lasts 30% of the tidal volume delivery time. This inspiratory hold timing can be adjustable or non-adjustable by the user or automatically by the machine by adjusting valve timing characteristics using the electronic board 506. Other variables that can be adjusted by the electronic board 506 or human-computer interface to modify ventilator function include, but are not limited to: PEEP, IPAP pressures, inspiratory timing, inspiratory flow rates, expiratory flow rates, expiratory timing, and/or $FiO_2$%. The PEEP may be algorithmically adjusted by the ventilator 1000 based on breath detection software time control. The breath detection software can generate PEEP predicted by pressure sensor 526 measurements by outputting tidal volume during last 10.0% of exhalation for example.

The ventilator 1000 can include a display interface (not shown) for displaying one or more parameters to a user. In one example, a simple LCD screen (not shown) configured as a display interface, may be used. As such, the ventilator 1000 may be configured as a "plug and play" device, not requiring connection to a monitor or other separate user interface. In such case, the flow rate of the input gas IG may be adjusted by the user, for example, in response to the information displayed to the user via the display interface. The ventilator 1000 may include a peak airway pressure sensor 1006 in fluid communication with the pressure sensor 526. The LCD screen may indicate, using a graphic or LED bar, when adjustments to gas source input flow should be made based on peak airway pressure sensor measurements measured by the peak airway pressure sensor 1006. Generally, gas source flow input should be increased when $SpO_2$ saturation is less than 90%, which can be measured using a separate patient/vital signs monitor and/or pulse oximeter and decreased when peak airway pressure is high (i.e., more than 35 cm $H_2O$). A fixed tidal volume delivered per breath can be provided to a user via the LCD screen or via a separate instruction manual based on adjustment of hospital wall $O_2$ supply flow rates. The user may increase tidal volumes delivered to a patient by increasing $O_2$ flow rate input at inlet 704. The inlet 704 may be an input gas source connector and may include a barb fitting, DISS connectors, quick connectors, and others. For example, the input gas source connector may be a ¼" NPT barb fitting that connects to a 50-psi hospital wall pipeline $O_2$ supply or $O_2$ tank using ¼" ID oxygen tubing. The inlet 704, the flow outlet airline 520, the breath detection airline 524, and an $CO_2$ exhalation conduit 1004 may include tubing connectors. For example, inlet 704, the flow outlet airline 520, breath detection airline 524, and an $CO_2$ exhalation conduit 1004 may include quick change connectors such that modifications to the patient circuit and/or gas source can be made, allowing components to be replaced. $CO_2$ exhalation conduit 1004 is in direct fluid communication with the $CO_2$ exhalation valve 1002 and is configured to receive exhalation gases from the user. The ventilator 1000 includes the air entrainment device 522, which in some configurations is a fixed $FiO_2$ based on mechanical design and hence should be easy to remove and replace in order for a user to adjust $FiO_2$.

Sensors, such as the pressure sensor 526 for measuring breathing characteristics and/or other aspects of patient physiology, may be either internal to the ventilator 1000 or external to ventilator 1000 and connected to patient interfaces, such as breathing flow sensors.

Examples of low tidal volume low PIF ventilation settings include, but are not limited to, as follows: 1) 5 LPM output flow rate, 150 ml tidal volume, 1.8 second tidal volume delivery duration; and 2) 40 LPM output flow rate, 750 mL tidal volume, 1.125 second tidal volume delivery duration The patient monitoring LCD number text display may include, but is not limited to, the following variables: tidal volume being delivered (mL), breathing frequency (BPM), I:E ratio, peak airway pressure (cm $H_2O$), PEEP (cm $H_2O$), gas source/$O_2$ flow rate input (LPM)

Control breathing can be output at a fixed time period, such as once every 6 seconds, for non-spontaneous breathing patients during that time period and can be used in a critical or non-critical care setting under the supervision of a trained physician for patients with ventilatory impairment. The ventilator 1000 can be used in adult, pediatric, and/or neonatal patient populations. The ventilator 1000 can also be used in homecare, hospital, ambulatory, and/or transport applications depending on configuration. With regard to detecting spontaneous breathing, exhalation is detected using breath detection software, which takes nasopharynx pressure sensor data measured from the breath detection airline 524 and uses mathematical formulas to predict whether a patient is going to transition from an exhalation to inhalation, which allows for the use of a pressure sensor significantly more sensitive than required in the ISO 80601-2-79 guidance. In one example, the pressure sensor may be up to six times (6×) more sensitive than required in the ISO 80601-2-79 guidance. This allows for PEEP of less than 5 cm $H_2O$ to be provided by the ventilator 1000 automatically, rather than relying on fixed pressure triggers as in many predicate devices, which sometimes fail.

Peak airway pressure is monitored using a peak airway pressure sensor 1006, with alarm conditions that trigger by the alarm 508 if certain pressure levels are reached such as 45 cm$H_2O$. Lung protective strategies with regard to patients with ARDS and this Assist Control ventilation are described. These include the use of low peak inspiratory flows and adjustable tidal volumes based on $O_2$ flow into the ventilator 1000, with indictors to the healthcare provider via the LCD display provided (not shown). This ventilation strategy is designed to support the patient work of breathing while minimizing the risk of high peak airway pressures that can cause ventilator-associated lung injury (VALI) or hypoventilation, while also promoting oxygenation by providing supplemental oxygen with a fixed 100% $FiO_2$ setting or same as gas source input to the patient and eliminating $CO_2$ from the patient circuit every single breath with no leakage and little resistance. In some embodiments, the FiO2 can also be adjusted or variable, either by the machine or user, by adding the air entrainment device 522, represented by FIGS. 1-4 and described in the specification.

The audible safety alarm 508 in the ventilator 1000 is designed for medical applications for use in ventilation equipment, certified that this audible safety alarm is recognized under the IEC 60601-1-8 standard. This alarm 508 is a component of the electronics board 506 that may include a specially designed speaker-housing assembly with no circuitry. Other alarm types can also be utilized including but not limited to: piezoelectric type speakers, audio amplifiers, and/or electromagnetic speakers. With this alarm 508, the OEM only needs to input a simple square wave signal with one frequency component, and the other needed harmonic sound frequencies are generated acoustically. This greatly simplifies implementation of an audible alarm sound in an IEC 60601-1-8 since the harmonic peaks are designed to be acoustically equal to the sound level required under IEC 60601-1-8. This alarm relies on the 2nd option for compliance, a melody table listed in Annex F of the IEC 60601-1-8 standard where specific medical conditions/applications are assigned individual melodies. These melodies are essentially little tunes that change in pitch per the tables in Annex F. The objective is that the medical personnel using medical equipment with alarms that use these melodies will become familiar with them which can help the medical personnel respond more quickly and more appropriately when a specific melody alarm sounds. This ventilator 1000 utilizes the alarm 508 to generate high, medium, or low priority warning sounds depending on the condition of the patient or malfunctions with ventilator equipment such as tubing disconnects. The audible sound has fundamental frequency<1000 Hz, with at least 4 harmonic frequencies within ±15 dB of the fundamental frequency. This alarm 508 has specific waveform and timing requirements for the three priority sounds, which includes a sound rise time specified by the alarm manufacturer. Alarm settings can include, but are not limited to, the following: if $O_2$ input from inlet 704 flows, but no breathing/exhalation is detected within 6 seconds, sound alarm—low priority; if the electrical power source 510 is being used—medium priority; if $O_2$ is connected in the wrong conduit (e.g., breath detection airline 524, flow outlet airline 520, or a $CO_2$ exhalation conduit 1004), sound alarm—high priority; if the pressure measured during inspiration using peak airway sensor 1006 is less than 40 cmH2O for more than 3 breaths in a row, sound alarm—high priority; if the $CO_2$ exhalation conduit 1004 gets disconnected from ventilator 1000 within 6 seconds of assist or control breath output, sound alarm—medium priority; if the flow outlet airline 520 gets disconnected from ventilator 1000 within 6 seconds of assist or control breath, sound alarm—high priority.

Figure 11:
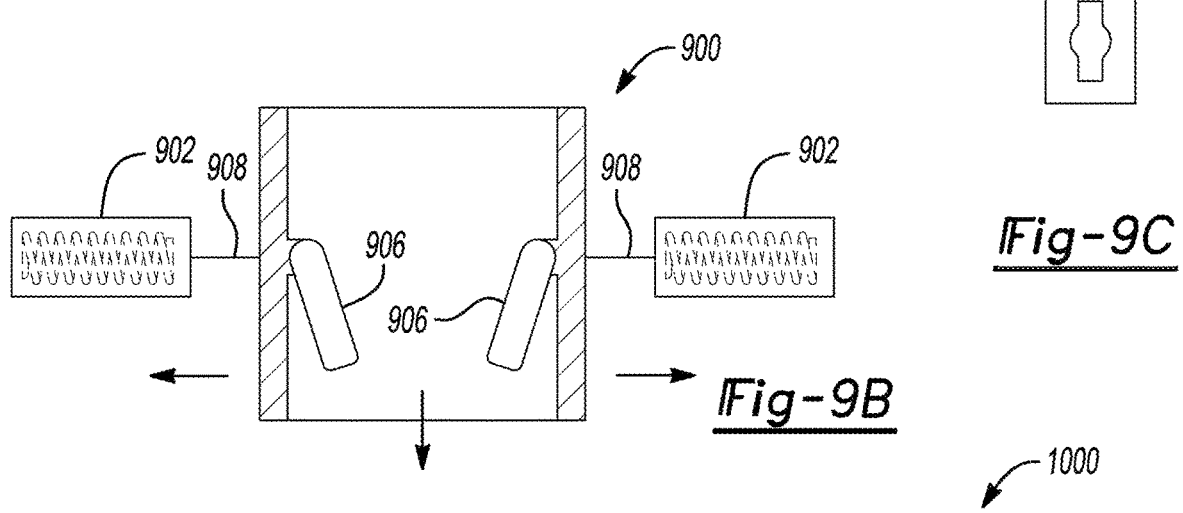
FIG. 11 is a schematic diagram of an invasive ventilator, wherein the carbon dioxide exhalation valve is inside the ventilator.
Figure 11:
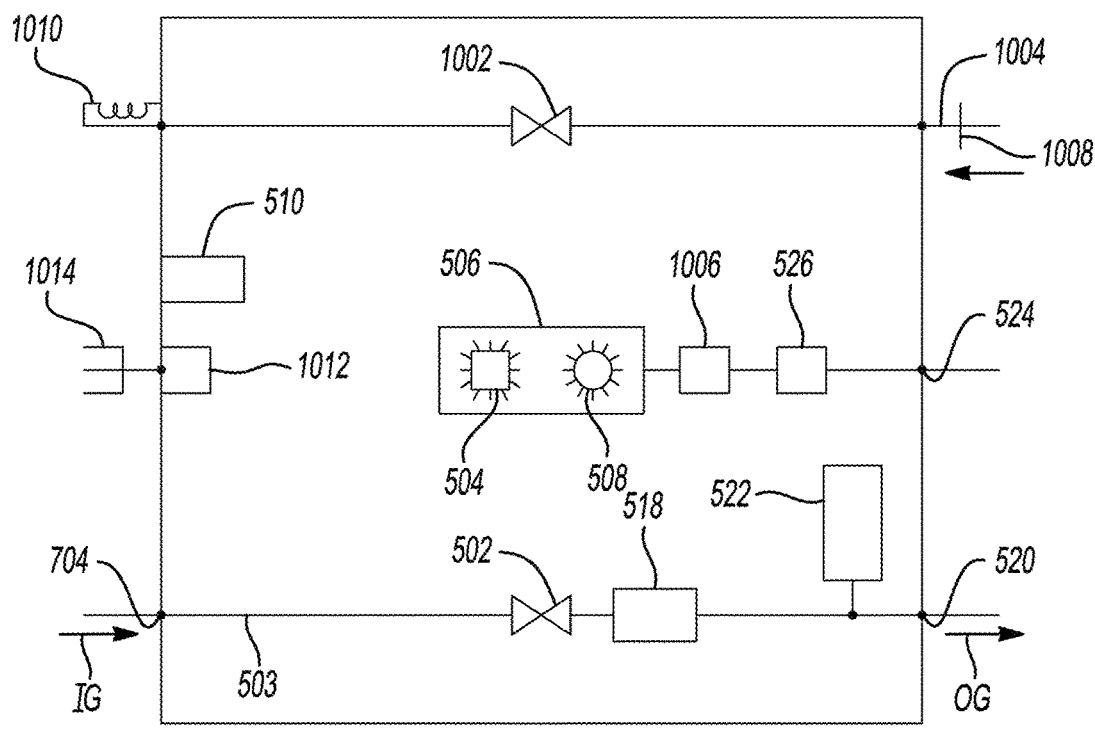

$CO_2$ rebreathing is minimized in accordance to the ISO 80601-2-79 standard through the use of a novel ultra-low resistance and leak free patient circuit shown in FIG. 11 that utilizes an active valve control inside the ventilator 1000.

Unlike other ventilators, no exhalation or inhalation valves are components of the patient circuit, but rather all control for inhalation and exhalation is performed inside the ventilator 1000. This is done using separate flow outlet airline 520 (i.e., an inspiration airlines) and $CO_2$ exhalation conduit 1004. The $CO_2$ exhalation conduit 1004 utilizes the $CO_2$ exhalation valve 1002, which may be: a solenoid valve with >6.5 mm orifice, a pinch valve that opens and closes 7 mm diameter tubing, and/or an electronically controlled check valve described in FIGS. 8-9, among others. This $CO_2$ exhalation valve 1002 allows for near zero resistance breathing since it is a similar diameter as a 6.5 mm endotracheal tube during invasive ventilation or intubation. Patient expired gas flows back through bacteria/viral filter 1008, which includes a 22 mm breathing tube connector to minimize exhalation resistance, before coming into contact with any internal device components. This viral/bacterial filter can feature standard coaxial ISO connectors (ISO 5356-1) that connect to standard breathing tubes using 15 mm ID/22 mm OD connectors for applications in breathing circuits, scavenging circuits, mechanical ventilation, and manual ventilation, including bag valve mask (BVM). This viral/bacterial filter 1008 is designed for single-patient use and, in some embodiments, can have bidirectional airline, be in-line, low flow resistance of 1.5 cm $H_2O$ pressure at 60 LPM, hydrophobic and electrostatic filtering properties, dead space of 45 mL, and ultrasonically welded. An HME filter or active heated humidification system and/or airline can be added to the flow outlet airline 520 to heat and moisturize the output gas OG output to the patient in order to prevent drying of airways and promote patient health/comfort. Patient gas is expelled to the atmosphere after bacteria/viral filtering through $CO_2$ exhalation valve 1002 and then an exhaust muffler 1010 that is in fluid communication with the $CO_2$ exhalation valve 1002. Other safety features related to exhalation are also implemented. One of which is that for example, the $CO_2$ exhalation valve 1002 is a normally open valve, which would allow the user to exhale even if the device malfunctions.

This ventilator 1000 utilizes an AC-DC converter (not shown), which is a 20 W high density and small size AC/DC module type medical grade power supply. It can operate between 80-264 VAC, has a low no load power consumption less than 0.075 W, and a high efficiency up to 87%. This AC-DC converter has Class II double insulation, high lifespan attributable to the interior potting, 5G anti-vibration, high EMC performance, 4KVAC isolation, etc. The AC-DC converter is designed by the manufacturer to meet IEC60601-1 and ANSI/AAMI ES60601-1 standards.

AAA Nickel Metal Hydride (NiMH) Rechargeable Batteries and an 8-battery holder may comprise the electrical power source 510. This is electrically designed to be a 12V circuit as a battery backup in case of main power supply failure, which makes the power electronics on the electronics board 506 simpler. The electrical power source 506 may be recharged after use by AC power module operation when the main power supply is back online. Each AAA cell is 1.2V with a rated capacity of 800 mAH. These alkaline batteries are safe and effective, used in millions of electronics devices across the world for over a decade. The battery cells may follow ANSI-1.2H1 and IEC-HR03 standards.

The ventilator 1000 may utilize an AC Power Module 1012 known as the Series DD12: IEC Appliance Inlet C14 with Filter, Fuseholder 1- or 2-pole, Line Switch 2-pole. Technical characteristics of this power module include: <5 µA (250 V/60 Hz) of current leakage, >1.7 kVDC between L-N and >2.7 kVDC between L/N-PE dielectric strength, front side IP40 protection according to IEC 60529, 1 or 2 pole fuseholder, Shocksafe category PC2 according to IEC 60127-6 for fuse-links 5×20 mm. The fuse drawer meets requirements of medical standard IEC/EN 60601-1. Further, this power module also includes a high frequency line filter as required under IEC 60601-1 as well as EMI filtering and Class X1- and Y1-capacitors. A line switch and power switch under Rocker switch 2-pole, non-illuminated, in accordance to IEC 61058-1 is also included. This power module 1012 is ideal for applications with high transient loads and electrical safety. The manufacturer of this power module has also stated that the aluminum case of the power module provides good EMI shielding, that all single elements are already wired, and that this power module is suitable for use in medical equipment according to IEC/UL 60601-1. A power receptacle 1014 connects to the AC power module to deliver wall power from a 120V or 240V source, depending on country of origin and/or use. The device utilizes a power receptacle or US Power Supply Cord with IEC Connector C13 with a V-Lock. This power cord is rated for 125 VAC, 50/60 Hz. This product is designed by the manufacturer to meet the following standards: IEC 60320-1, IEC 60320-3, UL 498, CSA C22.2 No. 42, IEC 60950-1.

Figure 15:
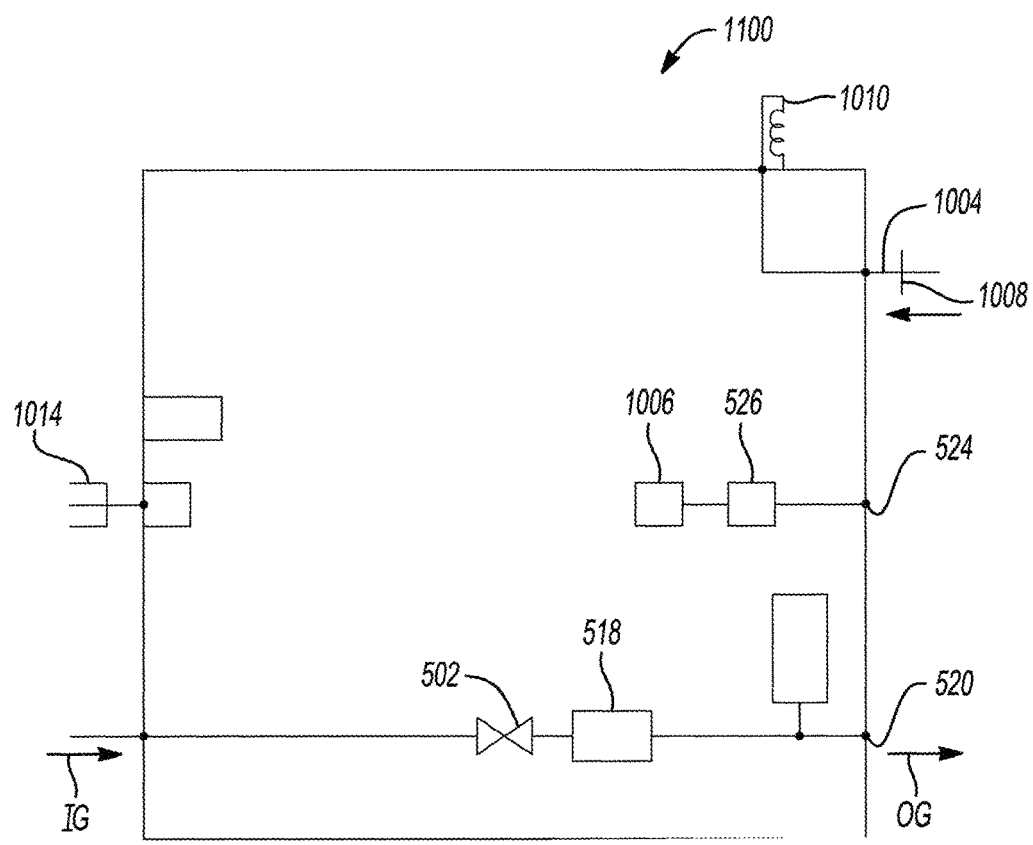
FIG. 15 is a schematic diagram of an invasive ventilator, wherein the $CO_2$ exhalation valve is inside the ventilator.

With reference to FIG. 15, a ventilator 1100 is similar to the ventilator 1000 shown in FIG. 11. However, one major difference is that there is no $CO_2$ exhalation valve in this configuration. For invasive ventilation in the configuration shown in FIG. 15, a single limb ventilator circuit would be required. This type of configuration would be more suited for ventilators with a focus on non-invasive home ventilation, where the capability of optional but less frequent use invasive ventilation is desired. This configuration without the active $CO_2$ exhalation valve inside the ventilator 1100 substantially reduces power consumption and weight compared to the ventilator 1000 shown in FIG. 11, allowing for lightweight portability with battery power.

Figure 16:
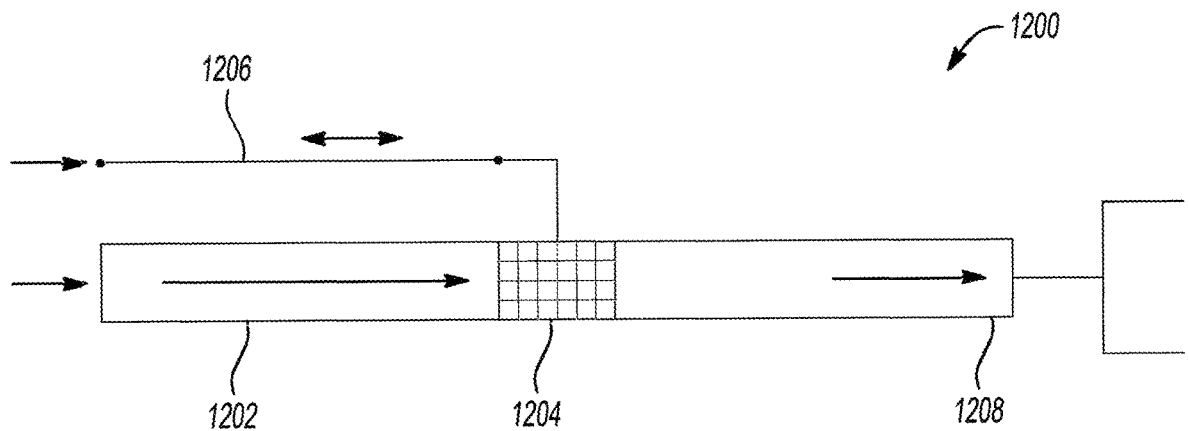
FIG. 16 is a schematic diagram of a non-invasive ventilator circuit using a breathing tube, an adapter, and oxygen tubing.

With reference to FIG. 16, a non-invasive ventilator circuit 1200 includes a breathing tubing 1202 (e.g., 22 mm tubing), an adapter 1204, an oxygen tubing 1206, and a patient interface 1208. This breathing tubing 1202 and any other tubing described herein can have various connector and inner tubing diameter sizes not specified in this disclosure. The inlet of the breathing tubing 1202 connects to the breath detection airline 524 to minimize flow resistance and measure breathing pressures (e.g., nasopharynx pressures) accurately without signal interference from the oxygen flow. The oxygen tubing 1206 would connect at the inlet of the tidal volume output airline flow outlet airline 520. The tidal volume from the ventilator 1100 would be output to the patient in a unidirectional flow from the inlet of the oxygen tubing 1206 to the barb inlet of the adapter 1204, and then to the patient interface 1208 either during a control or assist breath. The adapter 1204 is meant to serve as a connection point for the oxygen tubing 1206 and the breathing tubing 1202, allowing tidal volume flow output to the patient interface 1208 as well as bidirectional breath detection software data measurements using the 22 mm breathing tubing 1202 as a flow conduit to the sensors inside the ventilator, such as a nasopharynx pressure sensor 526 with a pressure measurement range of ±0.018 PSIG.

Figure 17:
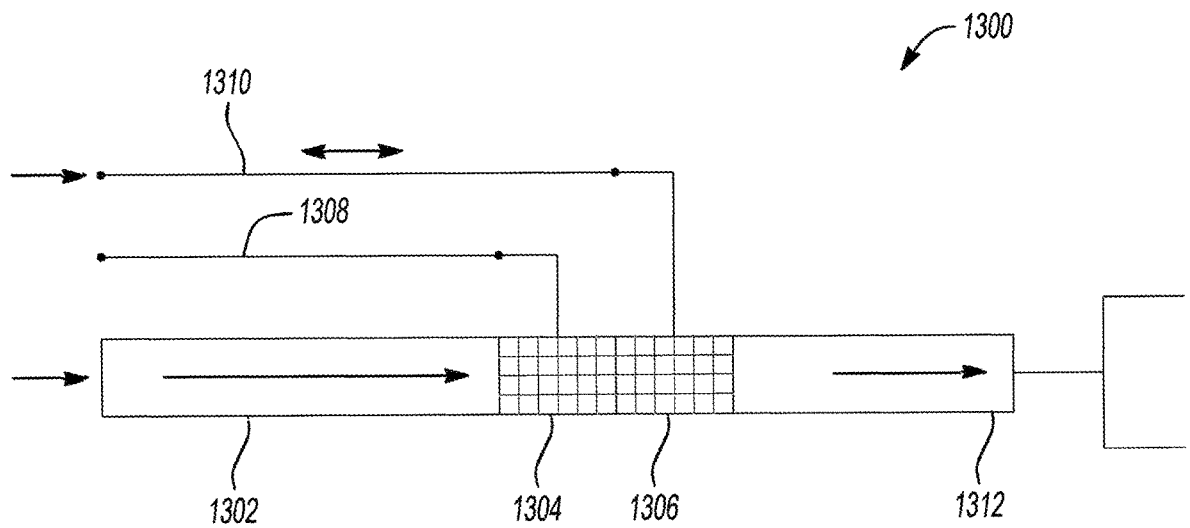
FIG. 17 is a schematic diagram of an invasive ventilator circuit using a breathing tube, an adapter, and oxygen tubing.

With reference to FIG. 17, an invasive ventilator circuit 1300 for the ventilator 1000 disclosed in FIG. 10 is described. This invasive ventilator circuit 1300 includes a breathing tubing 1302 (e.g., 22 mm tubing), adapter(s) 1304, 1306, oxygen tubing 1308, breath detection tubing 1310, and a patient interface 1312. This breathing detection tubing 1310 and any other tubing described herein can have various connector and inner tubing diameter sizes not specified in this disclosure. The inlet of the breathing detection tubing 1310 connects to the $CO_2$ exhalation conduit 1004 and/or viral/bacterial filter 1008 to minimize flow resistance during exhalation, which is actively controlled by the ventilator. The oxygen tubing 1308 is configured to be connected at the inlet of the flow outlet airline 520. The tidal volume from the ventilator 1000 would be output to the patient in a unidirectional flow from the inlet of the oxygen tubing 1308 to the barb inlet of the adapter 1304, and then to the patient interface 1312 either during a control or assist breath. The bidirectional breath detection software data measurements are taken using the breath detection tubing 1310. The breath detection tubing 1310 is connected to adapter 1306. As such, the breath detection tubing 1320 functions as a flow conduit to the sensors (e.g., pressure sensor 526 and peak airway pressure sensor 1006) inside the ventilator 1000. The adapter connector(s) 1304, 1306 can be separate or combined into one adapter. These adapter(s) peak airway pressure sensor 1006 serve as a connection point for the oxygen tubing 1308, 22 mm breathing tubing 1302, and breath detection tubing 1310. These adapter(s) 1304, 1306 allow tidal volume flow output to the patient interface 1312 as well as bidirectional breath detection software data measurements and active exhalation control without any sensor signal interference from different simultaneously occurring gas flows, such as breathing flows and/or tidal volume output from the ventilator 1000.

Figure 18:
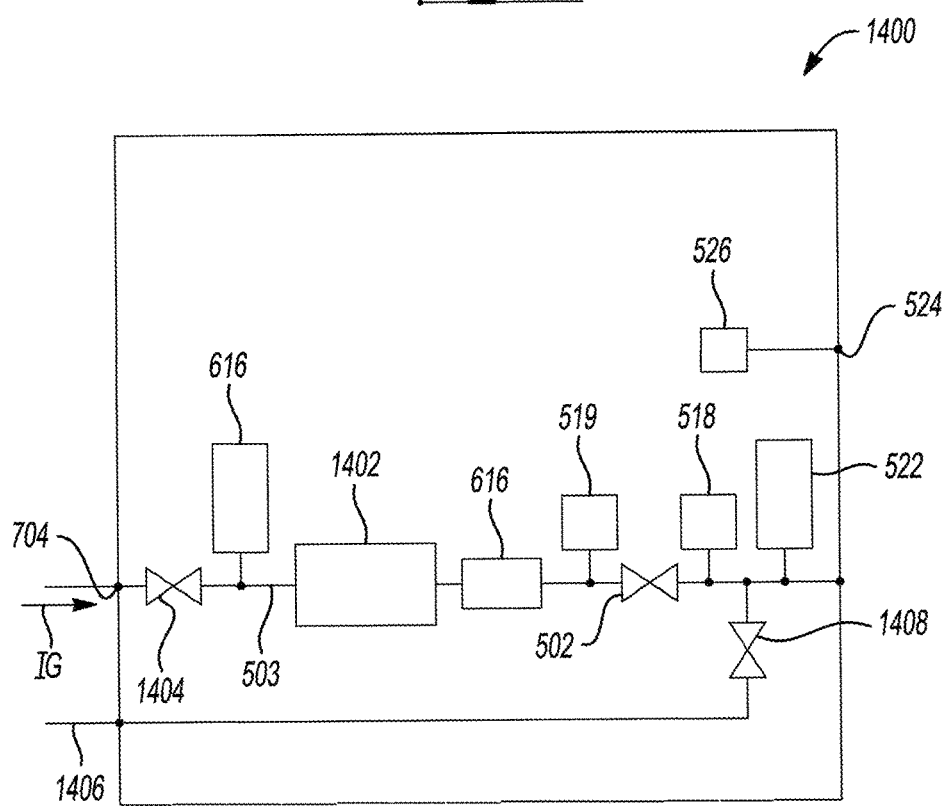
FIG. 18 is a schematic diagram of a ventilator with an internal oxygen concentrator that allows the use of an external gas source.

With reference to FIG. 18, a ventilator 1400 includes an internal oxygen concentrator 1402, which can be fluidly connected to allow external gas sources. This internal oxygen concentrator 1402 can be of several types, such as, but is not limited to: pressure swing adsorption, vacuum pressure swing adsorption, ultra-rapid pressure swing adsorption, oscillator pressure swing adsorption, "molecular gate" pressure swing adsorption, thermally cycled pressure swing adsorption, thermal swing adsorption, Joule-Thomson liquefaction units for the production of liquid oxygen from atmospheric air, gaseous oxygen tanks, liquid oxygen tanks, membrane based gas separation units, and combinations thereof. In a non-limiting example, the internal oxygen concentrator 1402 can be configured as disclosed in U.S. patent application Ser. No. 16/704,413, to which the current disclosure claims priority to, and benefit of, and which is hereby incorporated by reference in its entirety Several of these internal oxygen concentrators 1402 utilize an internal air compressor or blower unit (not shown). The ventilator 1400 may include inlet 704, which may function as an inlet source for gas source. This gas source may additionally include compressed air flow from an external blower or compressor fed to an internal air compressor or blower unit. The internal air compressor may be used to increase the pressure of the inlet gas IG, which, either due to the higher flows and/or pressures, can potentially increase the potential oxygen production flow rate of the internal oxygen concentrator 1402. This inlet 704 may be in fluid communication with a check valve 1404 to allow the inlet gas IG to be stored in an air volume tank 616. The air volume tank 616 may be external and/or internal to the ventilator 1400. The compressed air (i.e., input gas IG) may be fed directly to the gas separation media such as an adsorbent column. Further, in other embodiments, inlet compressed air can be used to drive a rotor that generates electrical energy to operate the system and/or recharge the batteries in addition or separately from AC wall outlet electricity. The ventilator 1400 may therefore be pneumatically and/or electrically powered. This can potentially be used to allow the internal oxygen concentrator 1402 to switch between a portable mode, wherein oxygen flow rates of around 5 LPM max are expected, and a stationary mode, where oxygen flow rates of 15 LPM or more can be produced.

The internal oxygen concentrator 1402 can be configured to detect when compressed air or other gas mixture is fed into the ventilator 1400. In response to detecting that the compressed air or other gas mixture is fed into the ventilator 1400, the ventilator 1400 shuts off or reduces the power usage of the internal air compressor, reducing energy consumption of the ventilator 1400 significantly during in-home use. When the oxygen concentrator 1402 is not producing 100% duty cycle continuous flow oxygen output, the air volume tank 616 may be used to store compressed air from either the internal air compressor or external air supply. When oxygen, for example, is not being produced using external compressed air from the inlet gas source, the compressed air can be used to create a Venturi vacuum using a Venturi vacuum generator (not shown) that improves the gas separation performance and/or allows for suctioning the patient using the ventilator 1400. The internal oxygen concentrator 1402 may produce continuous or intermittent flows of oxygen that do not synchronize with the user's breathing. To do so for example, the air volume tank 616 may be used to accumulate produced oxygen. This air volume tank 616 may also be used for sensor measurements, such as for measuring oxygen concentration purity percentage and/or flow rates of the $O_2$ output without using a flow sensor, such as the first flow sensor 518 and/or the second flow sensor 519. In some cases, one or more of the proportional valves 602, 605 are placed upstream of the air volume tank 616 to, for example, implement PI and/or PID flow control of the oxygen gas output. The air entrainment device 522 is used to augment the oxygen output with additional entrained room air, potentially reducing oxygen requirements for the user without requiring the use of an additional and/or separate air blower or compressor for air-$O_2$ mixing as done in other ventilators. The ventilator 1400 may include a separate outlet gas supply airline 1406 such that additional oxygen and/or compressed air can be fed into the ventilator 1400 from an external gas source, including but not limited to: oxygen tanks, portable oxygen concentrators, stationary oxygen concentrators, liquid oxygen tanks, air compressors, and/or air blowers. This separate outlet gas supply airline 1406 can be configured such that the gas accumulates in the air volume tank 616. Then, the air from the air volume tank 616 is received by the air entrainment device 522 and/or is controlled passively for output to the patient by check valve 1408 or actively by electronically controlled valve 502. This output of gas to the user is controllable by breath detection of spontaneous breathing using the breath detection airline 524 and, for example, the pressure sensor 526, and/or via ventilator machine settings such as control breaths for non-spontaneous breathing patients.

Figure 19:
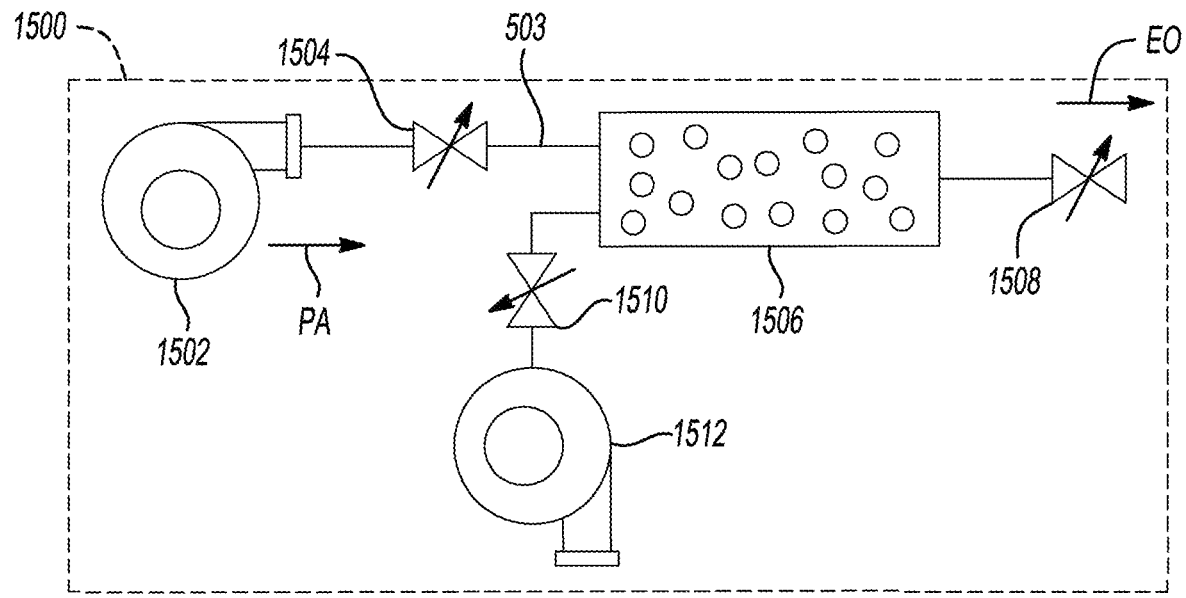
FIG. 19 is a schematic diagram of a vacuum pressure swing adsorption (VPSA) system using check valves for on-demand oxygen production during adsorption.

With reference to FIG. 19, a vacuum pressure swing adsorption (VPSA) system 1500 includes a plurality of valves for on demand or intermittent oxygen production. These valves could include but are not limited to the following valve types: check valves, electronically controlled solenoid valves, rotary valves, electronically controlled check valves, and valvular conduits such as Tesla valves. In some embodiments, a valveless PSA system could be created such that motor control allows the change in general pressure/flow directions from pressurization to depressurization flow through the modulation of power using a control method such as PWM, such that the motor control is implemented with one or more DC motor powered pumps and/or blowers, in some cases at high cyclical frequency such as 10 kHz. In some oxygen concentrators, pressure swing adsorption (PSA) is used to separate nitrogen from air using a zeolite adsorbent column in order to produce an enriched oxygen gas flow. This nitrogen must be desorbed from the adsorbent column at a cyclic frequency by reducing the pressure in the system to exploit the physical adsorption properties of the zeolite material, such as the adsorption isotherm and mass transfer coefficients. High pressure air compressors that produce in a range of between 1.5 to 2.5 atmospheres of pressurization may be used in other PSA systems to create the driving pressures required in other oxygen concentrator systems, because high pressure swing ratios are needed for several reasons. One primary reason is the fact that active valve control using electronic solenoid valves in other PSA systems has a high energy consumption, creates flow restrictions at low pressure, and inhibits high cyclic frequencies. With the use of high pressure swing ratios, longer adsorbent columns, which can also be characterized as adsorbent columns with length to diameter, or L:D ratios, greater than one, are generally used in order to prevent nitrogen breakthrough that generally occurs in shorter adsorbent column systems, which substantially reduces oxygen output purity. Also, with more zeolite material, the adsorption process can be run for longer before regeneration of the adsorbent column is required. Governing this phenomenon is nitrogen uptake kinetics or mass transfer. Adsorption kinetics is theorized to be highly logarithmic due to the electrostatic properties in the active Li+ ion sites in the zeolite crystalline structure, which can allow us to draw comparisons to parallel plate capacitors where charge accumulates much faster in the beginning. Generally, thinner zeolite laminates and smaller zeolite particle sizes increase the rate of mass transfer. Isotherm is also a physical characterization of adsorption. Isotherm represents the amount of gas adsorbed by zeolite at a fixed temperature as pressure increases. Further, to maintain high oxygen output purity and reduce the risk of adsorbent fluidization/nitrogen breakthrough, lower pressure ratios than other PSA systems can be utilized. This also means that in order to minimize the amount of zeolite adsorbent required to separate out a certain amount of gas, a high cycle time frequency should be used. As shown, Type I isotherms (such as those in the separation of $N_2$), are generally somewhat logarithmic in nature, with it being theorized that increases or decreases in pressure closer to absolute vacuum produce larger changes in adsorption quantities per unit pressure due to the Ideal Adsorbed Solution Theory (IAST) and the heat of adsorption.

With continued reference to FIG. 19, a PSA or VPSA system that uses pressure swing ratios less than 1.5 are used. An ultra-rapid VPSA system may be used and may include thin zeolite laminates instead of packed pellet beds in order to increase the rate of mass transfer, allowing faster cycle times and smaller PSA system, and reduce the pressure drop across adsorbent.

With continued reference to FIG. 19 the VPSA system 1500 is a passive valve pressure-controlled system designed to eliminate the use of active valve control that would create flow restrictions and inhibit high cyclic frequency rates. This gas separation method employed by the VPSA system 1500 is used to separate out nitrogen from air using a zeolite adsorbent column to produce enriched oxygen gas flow. In the VPSA system 1500, the cycle times are based on the electronic control of the ON/OFF switching frequencies of the blowers (MOSFETs may potentially be used), allowing for much higher cycle times than previous PSA architectures. Low cracking pressure check valves are used to control the direction of gas flows. The VPSA system 1500 includes a blower or air compressor 1502 and it functions by turning ON the blower or air compressor 1502 when oxygen output is desired. The ON/OFF timing of the blower 1502 can be determined via different methods including but not limited to: fixed cycle time frequency programmed into the blower motor controller or system microcontroller; breath detection during the useful phase of patient respiration, which can be variable in duration and/or during portion(s) of inspiration or expiration; variable cycle time frequency based on flow output characteristics demanded by machine settings or user breathing patterns. Cycle times for turning the blower 1502 ON/OFF can range between 2000 Hz to 10 seconds, and can depend on the latency of the power electronics inside the blower such as DC motors, pressurization/flow profiles of the blower output, and/or adsorbent column dimensions, mass transfer kinetics, and/or combinations thereof in order to optimize system performance for power density of oxygen production flow, energy efficiency of oxygen production flow, and/or flow rate of output desired. The VPSA system 1500 further includes a low cracking pressure check valve 1504 in fluid communication with the blower 1502 through the ventilator tubing 503. When the blower 1502 is ON, the pressurized air PA from blower 1502 flows through ventilator tubing 503 to the low cracking pressure check valve 1504. The VPSA system 1500 further includes an adsorbent column 1506 in fluid communication with the low cracking pressure check valve 1504. The adsorbent 1506 is downstream with the low cracking pressure check valve 1504. After flowing through the low cracking pressure check valve 1504, the pressured air PA flows to the adsorbent column 1506. The adsorbent column 1506 contains a zeolite adsorbent and desiccant. During adsorption as shown in FIG. 19, when the pressurized air flows through the adsorbent column 1506, the nitrogen from the pressurized air is adsorbed. The VPSA system 1500 includes a second check valve 1508 downstream of the adsorbent column 1506. Enriched oxygen gas EO existing the adsorbent column 1506 then flows to the second check valve 1508. The second check valve 1508 has a cracking pressure based on the pressure drop across the adsorbent column 1506 and hence outlet gas flow pressure.

Figure 20:
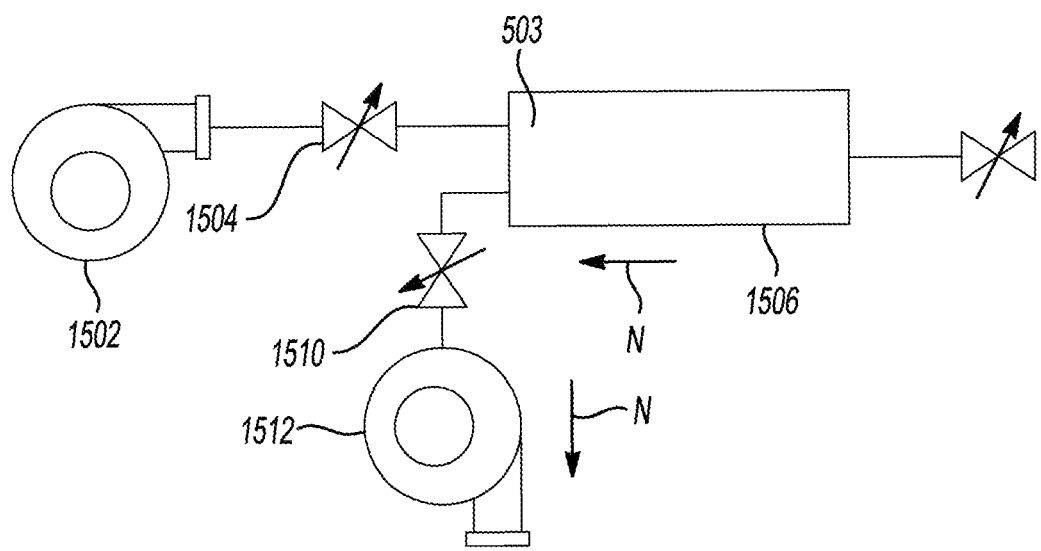
FIG. 20 is a schematic diagram of the VPSA system of FIG. 19 during desorption.

The VPSA system 1500 further includes a vacuum blower 1512 in fluid communication with the adsorbent column 1506. During desorption as shown in FIG. 20, the vacuum blower 1512 can be operated at variable ON/OFF cycle timing based on the same conditions as the pressurization blower 1502 or different conditions. Further, there can be overlap between the blowers ON/OFF cycles. In addition, the VPSA system 1500 also includes a vacuum check valve 1510 in fluid communication with the vacuum blower 1512. The pressurization blower 1502 will turn OFF, and then the vacuum blower 1512 will turn ON. As such, the vacuum check valve 1510 will OPEN to allow the nitrogen N to flow from the inlet of the adsorbent column 1506 to the vacuum blower 1512. The nitrogen N in the vacuum blower 1512 is then vented to the atmosphere or can be used for other purposes. When the vacuum blower 1502 is ON, the cracking pressure of the vacuum check valve 1510 would allow the vacuum check valve 1510 to be opened by the vacuum blower 1512, but at the same time only be able to be actuated by the vacuum blower 1512. The pressure from the pressurization blower 1502 at the inlet of the adsorbent column 1506 cannot open the vacuum check valve 1510. This vacuum check valve 1510 and the vacuum blower 1512 airline can be placed in a variety of different positions and/or using connectors, including but not limited to: T-connector, inlet or outlet tubing of adsorbent column 1506, separate adsorbent column 1506 connector at inlet, outlet, and/or other position in or around adsorbent column 1506 that is separate from other gas airlines. The second check valve 1508 and/or the other check valves 1504, 1508, 1510 may be a Tesla valve(s) such that there is no cracking pressure but rather flow is mostly unidirectional based on the flow resistance of the Tesla valve in a backflow scenario. The check valves 1504, 1510, 1512 may be electronically controlled check valves disclosed in FIGS. 8-9. The pressure output of the blower 1512 can be as low as 1 kPa with a cracking pressure of the check valve 1504 being as low as 0.9 kPa, with the cracking pressure of the check valve 1504 determined by the manufacturer of the VPSA system 1500 based on the flow rate and pressure specifications of the vacuum blower 1512. The blower(s) 1502, 1512 may also be electronically controlled using pulse-width modulation (PWM). Accordingly, the pulse widths of oxygen output during adsorption and desorption of nitrogen can be variable and optimized for certain flow rate output profiles, with different settings based on energy efficiency vs "power density" (oxygen production flow/lb weight of system) considerations. Further, the flow and pressure profiles of the blowers 1510, 1512 may be electronically varied per cycle by adjusting the motor speed in accordance with performance data. The blowers 1502, 1512 can have different pressure and/or flow profiles ranging in pressure from −30 to 30 kPa. Moreover, at least on of the blowers 1502, 1512 may operate with 100% duty cycle. As such, the VSPA system 1500 may include two separate inlet and two separate outlet airlines that are configured so that the blower can function as a dual pressure and vacuum pump, which can be electronically controlled in terms of switching functions between vacuum and pressure, flow rates, pressure, ON/OFF duty cycles, and/or other variables. The pulses of oxygen at less than 1 Hz frequency can be created by the VPSA system 1500.

A fast response flow sensor, such as the flow sensor 518, can be replaced with an air volume tank. In such a case, a pressure sensor (not shown) is used to measure how long it takes the take to get filled and then calculates based on the blower ON/OFF times (e.g., what is percentage duty cycle of the oxygen production) to then determine the output flow rate from the internal oxygen concentrator. Further, oxygen concentration-percentage purity sensors generally have a very slow (e.g., less than 4 seconds) response time and would not be able to detect the purity of a fast $O_2$ pulse (e.g., less than 100 ms). The flow sensor 518 can be used to measure how long it takes to fill an air volume tank to determine the $O_2$ flow rate and can also be used to allow $O_2$ to accumulate in the tank and measure $O_2$ purity percentage data readings. An ultra-fast response optical oxygen sensor or mass spectroscopy system can be created to measure the purity of each oxygen pulse.

Figure 21:
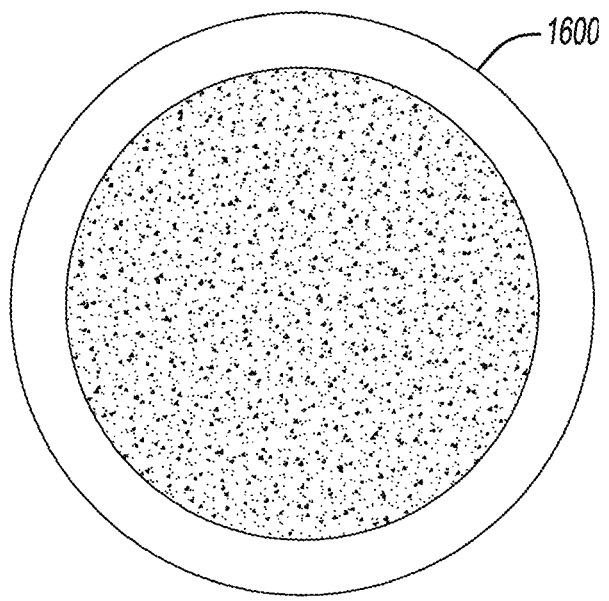
FIG. 21 is a schematic top view of a novel zeolite laminate adsorbent structure.
Figure 22:
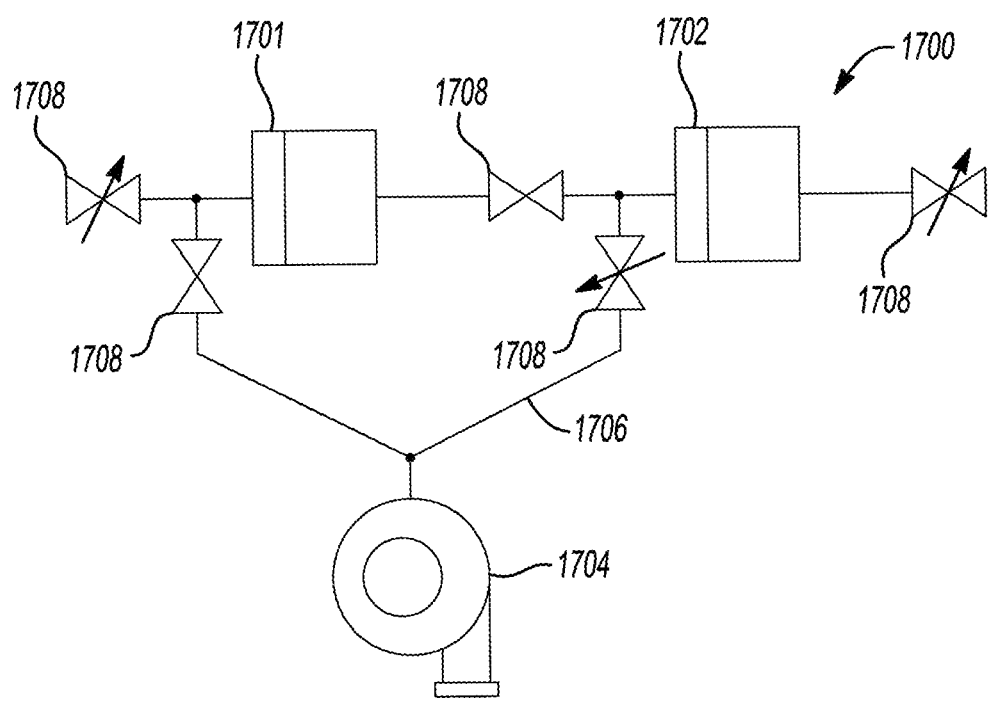
FIG. 22 is a schematic diagram of a system for making the structure of FIG. 21.

FIGS. 21 and 22 illustrate a novel zeolite laminate adsorbent structure 1600 and a system 1700 for making the same. The goal of this work is to create zeolite adsorbents that facilitate ultra-rapid pressure swing adsorption processes, and a PSA architecture that facilitates ultra-rapid cycle times and maximizes adsorbent productivity. This thin zeolite laminate may be manufactured using graphite dies and sintering of zeolite powder. Under high heat and pressure, it has been experimentally determined that zeolite pellets grounded into powder (with for example 0.2-50-micron particle sizes) can be formed into laminates under high pressure using a hydraulic press, for example 12 tons to produce 100 MPa compression, and 2000 degree C. temperatures without the use of binders that reduce adsorption performance, such as kaolin clay, by reducing the available surface area of the zeolite in the sintered structure. Different pressures and temperatures for creating the laminate can be used other than those stated above. This heating process can be in the form of rapid induction heating. This heating process binds the edges of zeolite compressed powder body to the 'melted metal' that comprises the adsorbent column 1506, which is then cooled and allows a bonded airtight seal around the zeolite laminate in addition to the press fit of the compressed powder body. Other materials can also be utilized for the adsorbent column including but not limited to: metals, thermoplastics, ceramics, and/or composite materials such as fiberglass reinforced plastics. Binders, such as kaolin clay, can be utilized. Ammonium bicarbonate or other pore former compounds can be introduced to add porosity to the compressed powder body, which can be removed during the heating process at 100 degrees C. in a vacuum-oven or other post-processing. This zeolite laminate can be manufactured as a compressed 'green body', which means that a mass of zeolite powder is compressed at high pressure and not heated. This 'green body' fabrication process is to maximize porosity, which sintering tends to reduce. The zeolite laminate can be directly molded inside a tube or mechanical structure that comprises the adsorbent column 1506, such that the zeolite laminate is never demolded. This reduces a concern found in experiments, where the zeolite laminate can collapse during demolding. In the fabrication of the zeolite laminate or porous body, techniques from ceramic sintering and powder metallurgy can also be utilized. To maximize the lifecycle of the $N_2$ adsorption zeolite, a desiccant filter (or desiccant material) 1701 should be placed before pressurized air encounters this $N_2$ zeolite. Water vapor and $CO_2$ substantially reduce the lifecycle of the $N_2$ adsorbent zeolite, which results in other adsorbent columns needing to be replaced.

The desiccant material 1701 can be in a variety of mechanical form factors including but not limited to pellet, filter, and/or laminate form. Generally, these $N_2$ zeolites generally include, but is not limited to, Lithium exchanged 5A or low silica X type zeolite. The desiccant material 1701 generally includes, but is not limited to: silica gel, activated alumina, and/or sodium based 5A zeolite. Two different material laminates can be in the adsorbent column 1506, one desiccant laminate and an $N_2$ adsorbent laminate. A single laminate can be created. For example, a bottom layer of the laminate may be placed at the inlet of the laminate and is a desiccant, and the middle/top layer of the laminate may be placed at the outlet of the laminate and is the $N_2$ zeolite adsorbent. The lifecycle of the zeolite adsorbent column 1506 may be increased by placing a desiccant laminate at the inlet distal end of the adsorbent column 1506 and placing an air gap between the $N_2$ adsorbent laminate, which is placed at the outlet end of the adsorbent column 1506. This air gap can also include a diffusion plate to slow down the gas travel. The goal of this air gap (with or without the diffusion plate) is to minimize the diffusivity of water vapor and $CO_2$ that decreases the lifecycle of the $N_2$ adsorbent material 1702. Further, the use of vacuum 1704 can also assist with removing water vapor and $CO_2$ at the inlet end of the $N_2$ adsorbent material 1702.

A separate airline 1706 can be added at the inlet distal end of the adsorbent column 1506 exclusively for water vapor/$CO_2$ removal from the desiccant material with the second vacuum airline being at the inlet end of the $N_2$ adsorbent zeolite laminate, which may be near the outlet distal end of the adsorbent column 1506. The water vapor/$CO_2$ removal from the desiccant laminate 1701 using a vacuum purge and $N_2$ removal from the $N_2$ adsorbent laminate using a vacuum purge can be separated using a check valve 1708 in combination with or exclusive of separated airlines. A long purge vacuum cycle can be used (for example 10 minute every 24 hours when VPSA system 1500 is not being used by a patient) to regenerate the adsorbent bed and remove as much water vapor/$CO_2$ as possible. This can also be a manual process by the user and instructed by the durable medical equipment (DME) or ventilator provider. This long purge vacuum cycle can also be used for the $N_2$ adsorbent column 1506 to maximize lifecycle. A heating and/or cooling element (not shown) can also be added to assist with this adsorbent column lifecycle maximization process by removing water vapor/$CO_2$ and/or $N_2$ through a long vacuum and/or heat purge process. This use of heating and cooling elements during the adsorption and desorption phases with small adsorbent columns can improve performance of the VPSA process and is known as thermally cycled PSA. The system 1700 can include additional check valves 1708 to control the flow in the circuit.

Figure 23:
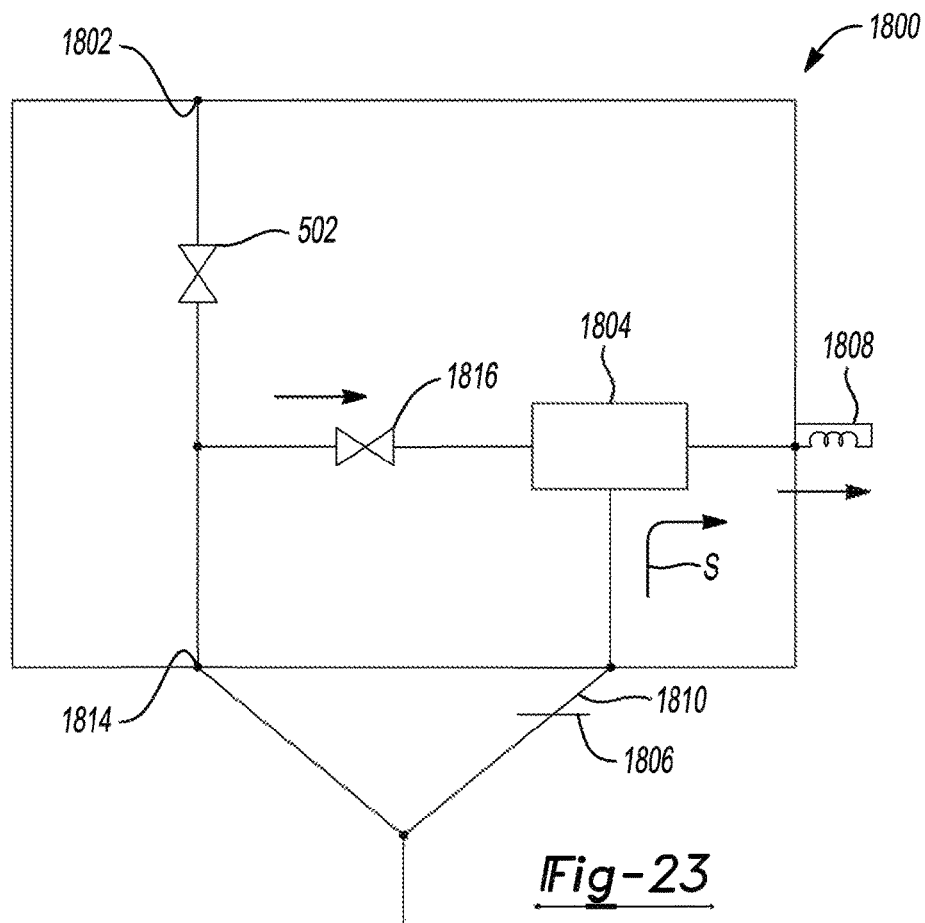
FIG. 23 is a schematic diagram of a ventilator with auto suctioning.

With reference to FIG. 23, a ventilator 1800 can function as a manually controlled and/or automated suctioning device. Suctioning is used to remove airway secretions commonly found in cystic fibrosis patients, as well as other patient populations that may or may not require ventilation. In many cases, invasively ventilated patients produce additional mucus since the trach tube bypasses the upper airway, which naturally warms and humidifies breathing air. In ventilated patients, this can necessitate periodic mucus removal from the tracheostomy tube to ensure proper breathing. Also, secretions left in the tube can become contaminated and a chest infection can develop. This suctioning generally takes place at vacuum pressures between 10-150 mmHg, depending on the patient and clinical application. Some hospitals use a centralized vacuum system that can be connected to a pressure regulator and then to the patient via a color-coded airline. Portable suctioning units also exist; however, these portable suctioning units generally operate at lower pressures such as 10-15 mmHg and/or use separate vacuum pumps or medical aspirators that are not integrated with a ventilatory support device. The ventilator 1800 may also be used as an airway clearance device such as a mechanical insufflation-exsufflation device, also known as cough assist. A mechanical insufflation-exsufflation device is designed to noninvasively clear secretions from the lungs by simulating a natural cough. Like a normal deep breath, this type of device applies positive air pressure (insufflation) to obtain a large volume of air within the lungs. The device then quickly reverses the flow of air by shifting to negative air pressure (exsufflation). The resulting high expiratory flow at vacuum pressures helps remove secretions out of the airway just like how a deep natural cough would.

The ventilator 1800 includes an inlet 1802 configured to receive compressed air or oxygen supply and a Venturi vacuum generator 1804 in fluid communication with the inlet. As such, the compressed air or oxygen supply from the inlet 1802 can flow to the Venturi vacuum generator 1804. In the ventilator 1800, the compressed air or oxygen supply is not being output as a tidal volume to the patient or insufflation, this compressed air or oxygen supply can be used to create a vacuum or exsufflation using the Venturi vacuum generator 1804 using the same gas source, similar to that disclosed in FIG. 4. The ventilator 1800 further includes a viral/bacterial filter 1806 in fluid communication with the Venturi vacuum generator 1804. The secretions S can flow through the viral/bacterial filter 1806 and exhausted through a nozzle 1808. The nozzle 1808 is downstream of the Venturi vacuum generator 1804. The viral/bacteria filter 1806 can be disposed in an exhalation airline 1810 that is connected to the Venturi vacuum generator 1804. The exhalation airline 1810 with viral/bacterial filter 1806 can be removed and a disposable tank for secretions (not shown) can replace the nozzle 1808. The Venturi vacuum generator 1804 may be user-replaceable using push-quick tubing connectors such that it can be replaced or sanitized by user and/or medical personnel on a periodic basis. A fluidic device or pump can be added to the exhalation/exsufflation airline 1810 to remove the secretions S. The exhalation/exsufflation airline 1810 may be separate from the normal exhalation airline described previously. Alternatively, the secretions S can be pumped out of the Venturi vacuum generator 1804 using fluid such as a liquid cleaning solvent periodically, for example once after every use and prevent clogging during repeated use. This compressed air or oxygen supply can be internal to the ventilator 1800 via an air blower or internal oxygen concentrator. Alternatively, the compressed air or oxygen supply may be an external gas supply, such as a 50 psi air compressor, compressed air supply in the hospital, a wall oxygen supply, an external oxygen concentrator, and/or an external oxygen tank or combination of internal/external gas sources hereof.

The Venturi Vacuum generator 1804 may be mechanically designed such that a lower pressure high flow input gas pressure source can be used to generate a higher pressure "deep" vacuum with lower flow. The vacuum pressure, flow rate, and ramp settings for insufflation and/or exsufflation can be adjusted by the user or machine based on a variety of factors including, but not limited to: device settings such as cough assist (non-invasive) or general suctioning (invasive), duration of suctioning therapy, triggering sensitivity or phase of breathing timing for insufflation and/or exsufflation, and/or pressure/flow ramp waveforms. An active valve control circuit can be used such that the compressed air/O2 from inlet 1802 or an internal gas source is output as a tidal volume to a patient via a valve 1816 and an inhalation/insufflation airline 1814, which in some instances can connect to a hose barb or 22 mm breathing tubing. The valve 1816 and the inhalation/insufflation airline 1814 are in fluid communication with the inlet 1802.

Further, the insufflation airline 1814 and the exsufflation airline 1810 can also be connected to the same single limb ventilator circuit using a wye connector (not shown). This compressed air/$O_2$ can then be routed to the patient during insufflation or as a tidal volume to the Venturi vacuum generator 1804 using an electronically controlled valve 1816. The Venturi vacuum generator 1804 would then create a vacuum or exsufflation that would flow through the exhalation airline 1810, based on the input compressed gas source supplied to the Venturi vacuum generator 1804. In the Venturi vacuum generator 1804, the compressed inlet gas plus vacuum generated and any resulting secretions would be extracted and then be exhausted out the nozzle 1808. The flow and/or pressure input from the compressed gas source can be controlled by the ventilator 1800 itself. For example, an internal $O_2$ concentrator can adjust motor speed to change output oxygen flow rate and pressures, which would affect the vacuum pressures and flows generated based on the mechanical design of the Venturi vacuum generator 1804. In other instances, the pressure and flow ramp profiles for exsufflation can be controlled (not by the input gas source) but rather using the valve 1816. The valve 1816 may be an electronically controlled proportional flow and/or pressure control valve. An air volume tank (not shown) and/or additional flow/pressure sensors can also be added to allow more precise control of these exsufflation flow/pressure characteristics. The electronically controlled proportional control valve 1816 can be replaced with a manual ball valve wherein a user can use a knob on the exterior of the device or human-computer interface such as touchscreen to create an orifice restriction that would slow down the flow of gas, decreasing the flow rate and hence the pressure/flow profiles of the exsufflation. This all can also apply to the control of insufflation to the user. An electronically or manually set valve at the vacuum inlet of the Venturi vacuum generator 1804 can be set such that the vacuum pressures and/or flow rates resulting from the inlet compressed air/$O_2$ from the valve 1816 can be adjusted manually by the user or automatically adjusted by the ventilator 1800. The Venturi vacuum generator 1804 can be used in combination with or substituted with a vacuum blower (not shown), such that the vacuum blower can be electrically controlled to turn ON during exsufflation, and OFF during insufflation. This ON/OFF switching, in some embodiments, can be controlled using MOSFET switch(es) or other means of electronic control.

Figure 24:
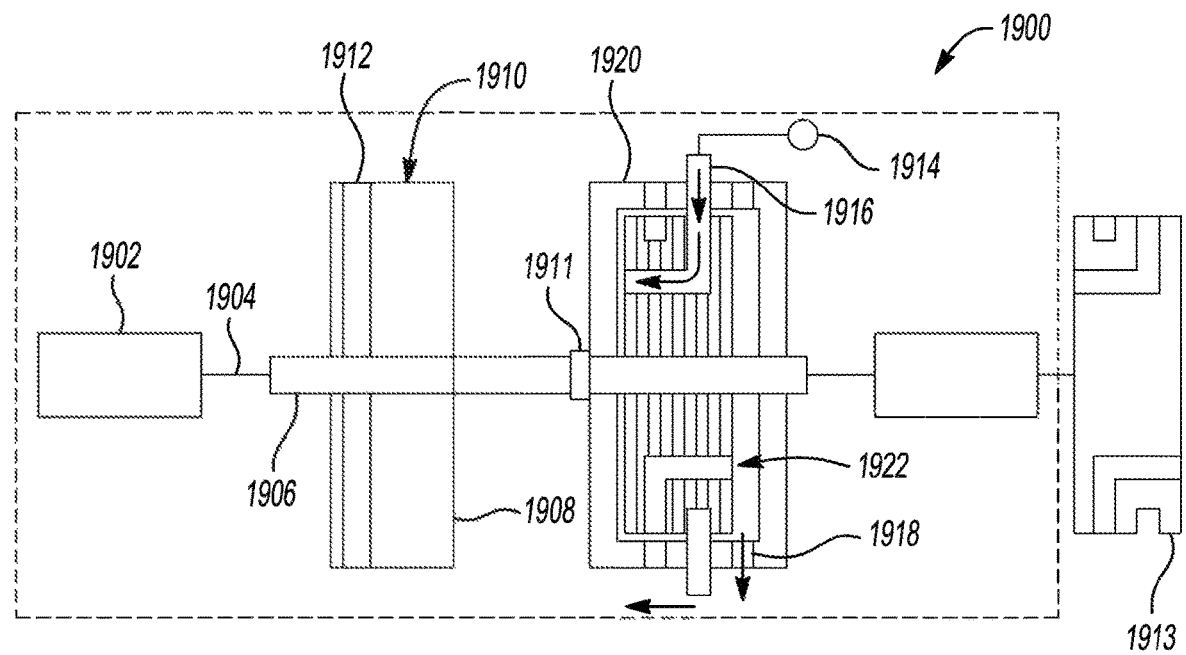
FIG. 24 is a schematic diagram of a mechanical oscillator pressure swing adsorption (PSA) and high frequency ventilation system.

With reference to FIG. 24, a Mechanical Oscillator pressure swing adsorption (PSA) and High Frequency Ventilation system 1900 is described. The goal of oscillatory PSA system 1900 is to allow the use of ultra-rapid cycle times with minimal flow resistance, thereby reducing fluid pressure requirements and eliminating the need for check valves or active valve control. Instead, the valve control or even electronic ON/OFF control of blowers are replaced with motion control of actuator(s) 1902, which can include but are not limited to: electromagnetic solenoids, linear motors, DC motors with gear mechanisms to convert rotary motion into linear motion, piezoelectric actuators, hydraulic actuators, pistons, servo motors, and/or air cylinders. In addition to the actuators 1902, the ventilation system 1900 includes an actuator shaft 1904 coupled to the actuator 1902 and an oscillator shaft 1906 coupled to the actuator shaft 1904. The oscillator shaft 1906 can be accelerated via the forces exerted by the actuator 1902 via the actuator shaft 1904. A short push-pull stroke and high frequency actuations can be used to create high frequency oscillations. The actuator shaft 1904 can be combined with an air spring 1908 or actual spring, such that a recoil force can be mechanically generated once the oscillator shaft 1906 travels a certain distance. This distance can be controlled mechanically based on the dimensions of the spring housing 1910 and/or the spring coil 1912. The air spring 1908 can be eliminated by using electronic position and/or motion control of the actuator 1902. For example, a precision feedback closed loop algorithm(s), such as PID control, can be implemented such that the acceleration of the actuator shaft 1904 can be measured and allow for precision position control (with for example 0.1 mm positioning accuracy) compared to predictions. This can allow for the implementation of an oscillatory PSA system 1900 such that two or more opposing actuators can be actuated in a pulsating manner such that the system operates at resonance frequency. This can be optimized using electronic control such that oxygen performance is maximized, and noise of the system is minimized. Accelerations and decelerations of the actuator shaft 1904 can also be variable, such that the actuator shaft 1904 can accelerate faster than it would decelerate, varying the times of adsorption and desorption, which can be controlled using for example PWM. The oscillator shaft 1906 can be coupled to ball bearing(s) 1911, such that less force is required to accelerate and decelerate the oscillator shaft 1906. A piston 1913 can be mechanically designed, such that fluid can flow through the piston 1913 in a certain geometric pattern. The fluid can be inputted or exhausted via certain ports/air channels that comprise the piston 1913. The piston 1913 can be manufactured using a variety of manufacturing methods including, but not limited to: 3D printed, machined, molded, cast, and/or fabricated as one or more assembled components using one or more materials including but not limited to aluminum, titanium, stainless steel, thermoplastic, composites, and/or polymeric materials.

The PSA system 1900 can also be designed such that piston 1913 uses air seals instead of lubricants, such that loose tolerances would be required to create pressurization/depressurization cycles such that it is mainly dependent on the geometric design of the piston 1913. Pump assemblies and additional pistons in series or in parallel can be operated to amplify pressure, flow, and/or frequency of the overall system. The piston 1913 can be attached and/or a component of the oscillator shaft 1906, such that the piston 1913 oscillates at the same speed and direction as the oscillator shaft 1906. An air blower or air fan 1914 can be included in the PSA system 1900 to drive air into the air intake port(s) 1916. The location and size of the intake port(s) 1916 and exhaust port(s) 1918 are based upon the mechanical design of the enclosure 1920. The air blower or air fan 1914 can be microscale, nanoscale, ducted, and/or heat exchanged.

In the position shown in FIG. 24 low pressure or ambient air from the air fan 1914 flows through the intake port(s) 1916 and one or more air channels that comprise the oscillator piston 1913. One or more air channels that comprises the piston 1913 allows gas flow to a layer of zeolite adsorbent 1922. In this position, the oscillator piston 1913 compresses an amount of this gas, separating out nitrogen from the intake air. The oscillator shaft 1906 then moves in the opposite direction. As a result, the volume between the oscillator piston 1913 and the layer of zeolite 1922 expands, reducing the pressure in the system while simultaneously the piston 1913 travels such that the nitrogen gas can be released from the zeolite via exhaust port(s) 1918. The oscillator piston 1913 can comprise two halves wherein the air channel (s) and exhaust port shape(s) are in perpendicular and/or opposite directions from each other. The enclosure 1920 contains a second layer of $N_2$ or zeolite adsorbent 1922, such that two separate adsorption and desorption cycles occur each back and forth piston stroke. This overall oscillatory PSA system 1900 can facilitate the use of ultra-low pressures, such as less than 1 cmH2O pressure, as well as ultra-fast cycle times (for example more than 1000 Hz) using precision machining, additive manufacturing, microfabrication techniques, and/or a combination of technologies thereof. This oscillatory PSA system 1900 can be used to generate oxygen as an internal oxygen concentrator and/or as a gas source for a ventilator with different ventilation modes including but not limited to: Assist Control, Volume Control, Pressure Control, SIMV, Volume Assist, PAV, and/or high frequency ventilation. The oscillatory PSA system 1900 is used as a high frequency ventilator, such that tidal volume or $O_2$ output is produced at a high frequency, such as more than 10 Hz. A mean effective pressure (MEP) is generated by the oscillatory PSA system 1900. The MEP can also be measured and/or controlled using, for example, varying the pulse widths and/or peak airway pressure sensor measurements. This can be used in combination with or separate from an air entrainment device 522. Further, the heat engine of the PSA system 1900 can be designed that the PSA cycle operates similar to reciprocating and/or linear heat engine designs, wherein the combustion process with fuel injection/ignition would be replaced with zeolite adsorbent(s) and mechanical energy is input instead of created. Examples of PSA heat engine architecture designs include the diesel cycle, Wankel cycle, free linear pistons, Otto cycle, and/or jet turbines. Energy input sources can include electric motors, hydraulic actuators, planetary gears, other mechanisms of converting motion, and/or heat engines that combust fuels such as hydrocarbons, alcohol, and/or biofuels. Further, the oscillator piston 1913 can create motion including but not limited to the following motion patterns: sinusoidal, toroidal, rectilinear, rotational, and/or wave patterns.

Figure 25A:
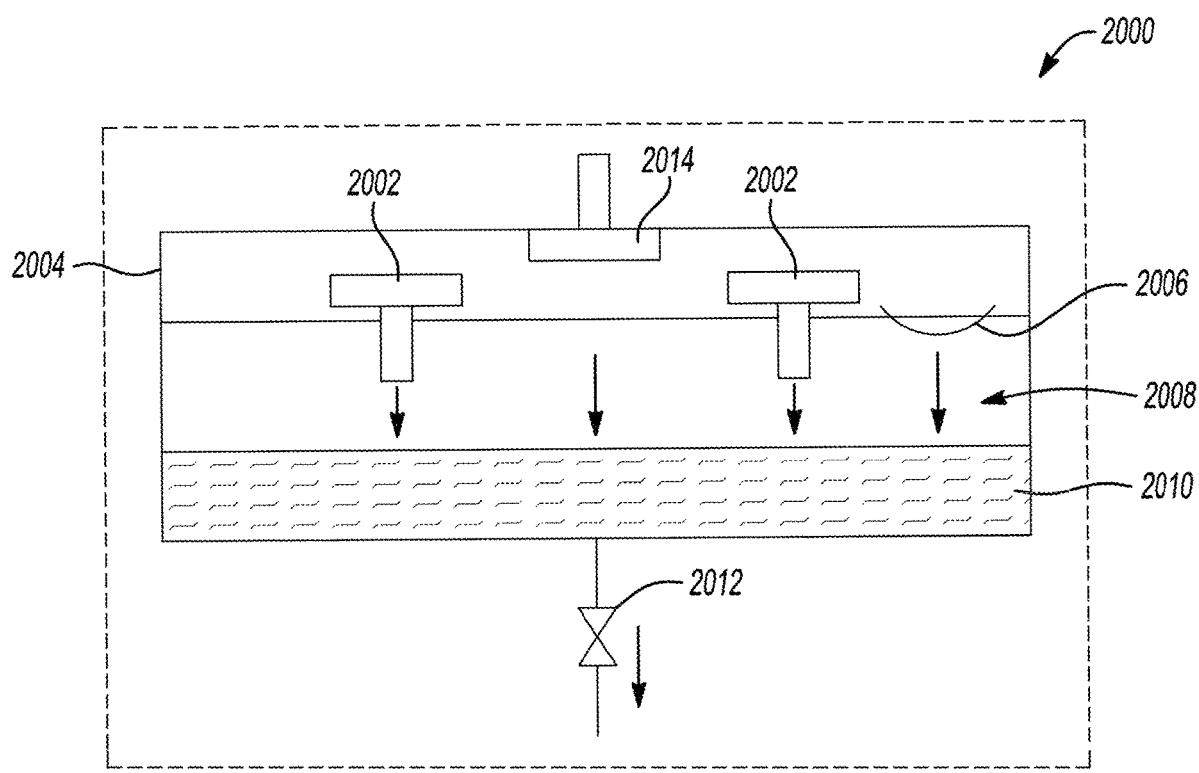
FIG. 25A is a first schematic diagram of a piezoelectric oscillator PSA and high frequency ventilation system.
Figure 25B:
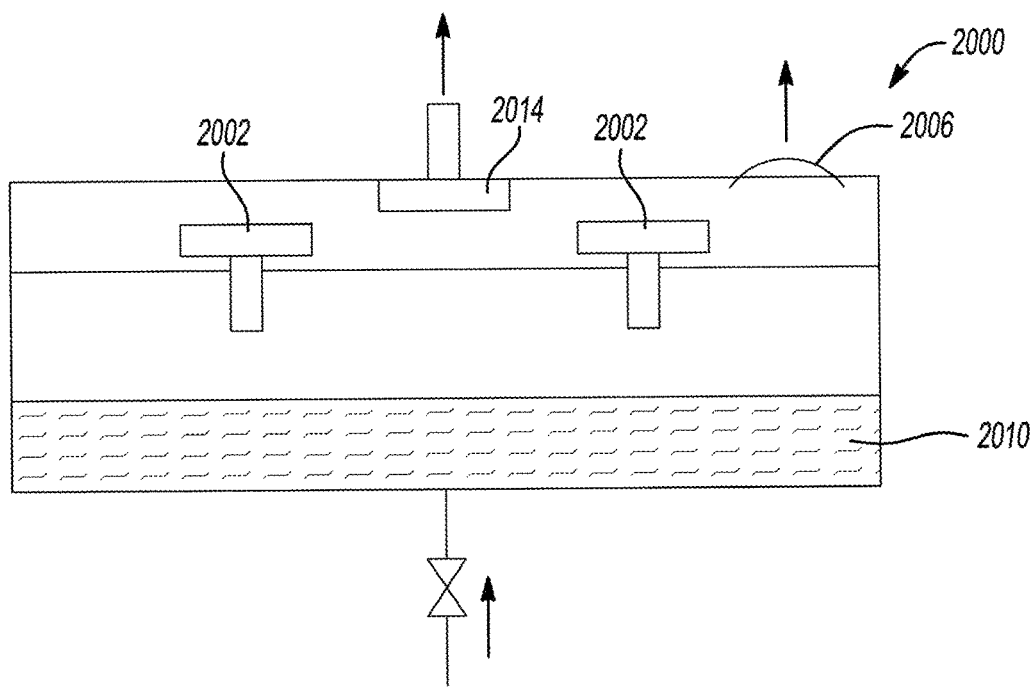
FIG. 25B is a second schematic diagram of a piezoelectric oscillator PSA and high frequency ventilation system.

With reference to FIGS. 25A and 25B, a piezoelectric oscillator PSA and high frequency ventilation system 2000 is described. The piezoelectric oscillatory PSA system includes piezoelectric microblowers 2002, which are surface mounted to a printed circuit board 2004. The piezoelectric microblowers 2002 include a piezoelectric oscillator element 2006 that vibrates at, for example 28 kHz, and an integrated check valve (not shown). When the piezoelectric oscillator 2006 oscillates back and forth, a unidirectional pressure/flow is produced. The vibrations of this piezoelectric oscillator 2006 can be electronically controlled such that the pressures, flows, and oscillatory frequency can be varied based on electrical response to changes in voltage and/or power. PWM can be used to control the frequency of the piezoelectric oscillator 2006, such that the oscillator 2006 can be accelerated and decelerated at different or the same speeds. Each individual piezoelectric microblower 2002 can be controlled individually or as a group of two or more blowers operating in series and/or parallel. The piezoelectric microblowers 2002 can be mounted in an enclosure, such that with two microblowers 2002, for example, the pressure output can be doubled for example from 2 kPa to 4 kPa, while keeping flow the same as one microblower. Further, electronic control can be used such that full depressurization and pressurization cycles can be achieved. For example, MOSFET switches (not shown) can be used to turn the blower(s) 2002 ON or OFF. As such, the microblowers 2002 can be electronically controlled such that the oscillator element 2006 will not turn OFF mid-oscillation when vibrating at high frequency such as 28 kHz, but rather will wait to turn OFF until the end of an individual oscillation. One or more microblowers 2002 can be used for pressurization during the adsorption cycle while a separate set of reverse microblower(s) 2002 can be used to produce vacuum during the desorption cycle. Alternatively, the piezoelectric oscillators 2006 can be used to replace or in combination with the piezoelectric microblowers 2002. The piezoelectric oscillators 2006 can be used to produce high frequency pressurization and vacuum, moving very small amounts of gas per oscillation. Electromagnetic or other types of oscillators can also be used.

With reference to FIG. 25A, the piezoelectric oscillator PSA system 2000 functions by turning ON a set of pressurization microblowers 2002, which pressurize an air chamber 2008. This compressed air then flows through a zeolite adsorbent 2010, which can be a variety of mechanical structures including but not limited to pellets, laminates, microfabricated thin films, and/or porous honeycombs. The nitrogen from the pressurized air is adsorbed by the zeolite, producing an enriched oxygen flow that flows out a valve 2012. The valve 2012 may be passively controlled such as a check valve, actively controlled using electronics such as a solenoid valve, and/or a combination thereof.

With reference to FIG. 25B the desorption cycle then occurs. Thus, the pressurization microblowers 2002 are then turned OFF, and the vacuum microblowers 2014 are turned ON. As a consequence, the nitrogen is removed from the zeolite adsorbent 2010 and vented to the atmosphere.

This adsorption and desorption process can be performed at a high cyclical rate, in some cases in excess of 14 kHz. There can be overlap between these two phases such that the sets of pressurization microblowers 2002 and vacuum microblowers 2014 can both be OFF or ON at the same time. Only one set of microblowers 2002 can be used. For example, air blowers, external and/or internal, can be used to drive air into the PSA such that only a set of vacuum microblowers 2002 is used, making the system a vacuum swing adsorption or VSA cycle. Only a set of pressurization microblowers 2002 and no vacuum microblowers 2014 would be used, such that the system 2000 is a true PSA architecture. In such a case, atmospheric or oxygen purge would be used to remove nitrogen from the zeolite adsorbent 2010 during the desorption phase. These pressures and/or flows from the microblowers 2002, 2014 for pressurization and depressurization can also be similar or different values. A Tesla valve can be used as the valve type for valve 2012, such that a certain percentage of the oxygen from an air volume tank (not shown) can be recirculated during the purge process in the desorption phase. This percentage of oxygen recirculation is variable based on the mechanical design of the Tesla valve and backflow resistance.

Figure 26:
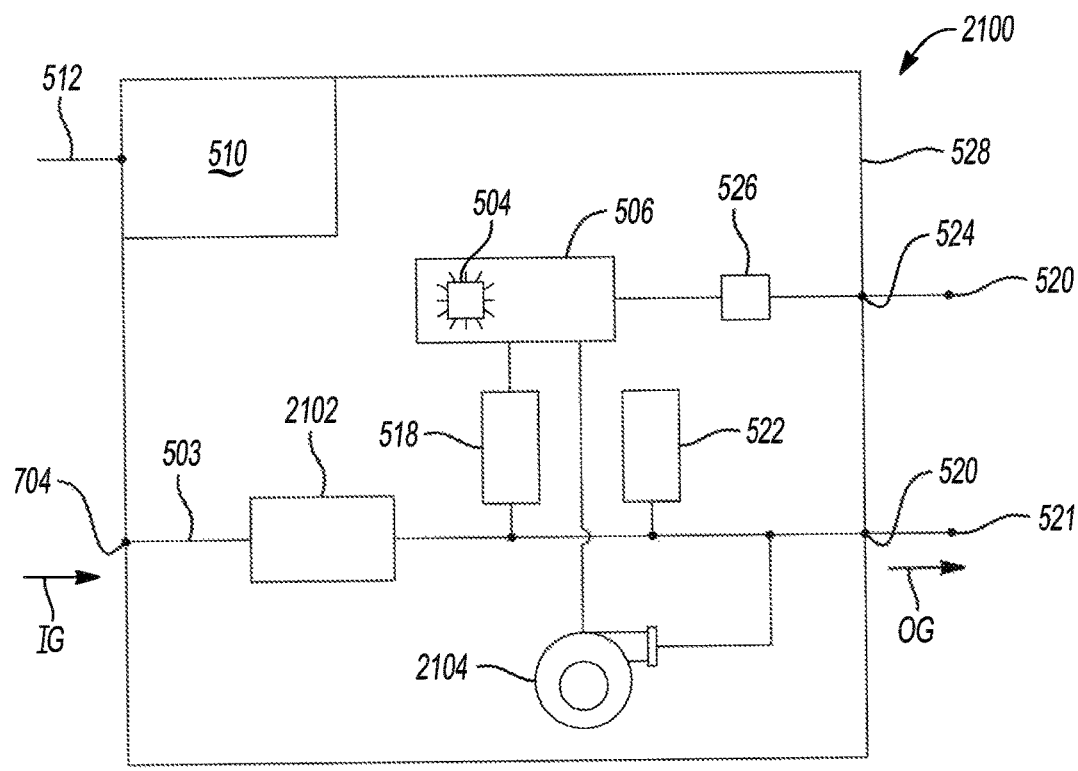
FIG. 26 is a schematic diagram of a ventilator that can function as BiPAP or CPAP device, an $O_2$ concentration, and/or ventilator with different modes.

FIG. 26 illustrates a ventilator 2100 that can function as a bilevel positive airway pressure (BiPAP) device or continuous positive airway pressure (CPAP) device, oxygen ($O_2$) concentrator, and/or ventilator 2100 with different modes. The ventilator 2100 includes an enclosure 528, a tubing 503 configured to receive the input gas IG, and an internal oxygen concentrator 2102 in fluid communication with the tubing 503. The tubing 503 is entirely or at least partially disposed inside the enclosure 528 to minimize the space occupied by the ventilator 2100. The internal oxygen concentrator 2102 is integrated with the ventilator 2100 and is therefore entirely disposed inside the enclosure 528 to minimize the space occupied by the ventilator 2100. The internal oxygen concentrator 2102 can be used to generate enriched oxygen flow to the patient (i.e., output gas OG). The internal oxygen concentrator 2102 can be turned ON or OFF either automatically using electronic control from the controller 504 (e.g., a microcontroller unit) or via user adjustment of a human-computer interface, including, but not limited to, knobs, touchscreens, and/or switches. The internal oxygen concentrator 2102 can produce and/or deliver oxygen on demand based on a patient's breathing needs, provide a continuous flow of oxygen, and/or produce an oscillatory or irregular oxygen output pattern to the user via the flow outlet airline 520.

The ventilator 2100 may include air entrainment device 522 in fluid communication with the internal oxygen concentrator 2102. The enriched oxygen exiting from the oxygen concentrator 2102 may be used to entrain room air using the air entrainment device 522. The ventilator 2100 may additionally include an air blower 2104 in fluid communication with the internal oxygen concentrator 2102. The air blower 2104 may be in communication with the controller 504. The controller 504 can be programmed to adjust the output gas OG to the patient by the air blower 2104. The air entrainment device 522 could be substituted for or used to perform air-$O_2$ mixing. In some embodiments, oxygen could be delivered to the patient during useful phases of respiration as measured using the breath detection airline 524 and the pressure sensor 526. After oxygen is delivered during the useful phase of respiration, a PEEP could be provided using the air blower 2104 to prevent lung collapse in patients with chronic lung diseases, especially those who are mechanically ventilated. This output pressure from the air blower 2104 may be controlled using the controller 504 or via user input from a human-computer interface 2406 (FIG. 27B), at specific ranges for example 0.1-20 $cmH_2O$ pressure. The output flow (e.g., output gas OG) may also be controlled using the controller 504. For example, the controller 504 may control the output gas OG by controlling the blower motor speed of the air blower 2104, voltage, and/or power consumption of the ventilator 2100. In some embodiments, an additional pressure sensor can be added to the outlet airline 520 to measure the output pressure of the output gas OG to the patient.

In some embodiments, the pressure of the output gas OG provided to the patient may be controlled by the controller 504 or the user. The air blower 2104 may control the output airflow (e.g., output gas) to modulate the pressure based on a setpoint. For example, if the output pressure of the $O_2$ and/or compressed air tidal volume from the airline 520 is 6.8 $cmH_2O$ at a flow of 40 LPM and the setpoint is 3.9 $cmH_2O$, the air blower 2104 can output 1 $cmH_2O$ pressure at 40 LPM flow to achieve the setpoint. In some embodiments of the invention, oxygen pulses could be output intermittently at a frequency greater than an inhalation frequency. In some embodiments, during a period of useful respiration one or more pulse(s) of oxygen could be output followed in terms of timing by one or more pulse(s) of air from the air blower 2104. The lengths of these oxygen and/or blower air pulses can be different or the same as each other.

In another embodiment, the air blower 2104 may be used as an integrated or separate BiPAP/CPAP machine, wherein modes and settings could be selectable, deactivated, and/or activated by the user, healthcare provider, and/or DME based on payment/billing code. For example, the DME supplier may remotely, using software only, enable the ventilator 2100 for use as a non-invasive ventilator if the patient were only prescribed a non-invasive ventilator. If a patient, however, requires supplemental oxygen one year later, the DME can remotely enable this feature using software and then subsequently bill Medicare or an insurance provider for that add-on. In some embodiments, this can also include integrated oxygen and CPAP for obstructive sleep apnea patients with overlap syndrome.

In some embodiments, the blower pressure of the air blower 2104, including IPAP and PEEP, can be controlled by the user, clinician, and/or healthcare provide, with the settings recommended or based on the patient prescription and/or real time physiological characteristics such as breathing, pulse oximetry data, vital signs data, etc. For BiPAP, this generally means that the pressures of the air output can range between 5-20 $cmH_2O$ IPAP, and at least 3 cmH2O less for PEEP, for example 2-17 cmH2O PEEP. These IPAP and PEEP variables may be independently or jointly controlled, by the machine software itself, clinician, and/or user. For CPAP or IPAP, the pressure for IPAP and PEEP would be the same. Hence, only one pressure setpoint would be set. In one embodiment, tidal volume and flow rates of the air blower 2104 could also be controlled by the controller 504 (e.g., microprocessor) of the ventilator 2100, a clinician, and/or the user to maximize user comfort, with guidelines based on the patient interface used which could vary from user to a user based on patient physiology and mask leakage. This PEEP could also be determined based on peak airway pressure or predicted using the breath detection software. In some embodiments of the invention, the ventilator 2100 can also include wireless communication technology and/or features that allow the ventilator 2100 to function as an at-home sleep test, and/or at-home oxygen test, and provide patient monitoring for the clinician.

Figure 27:
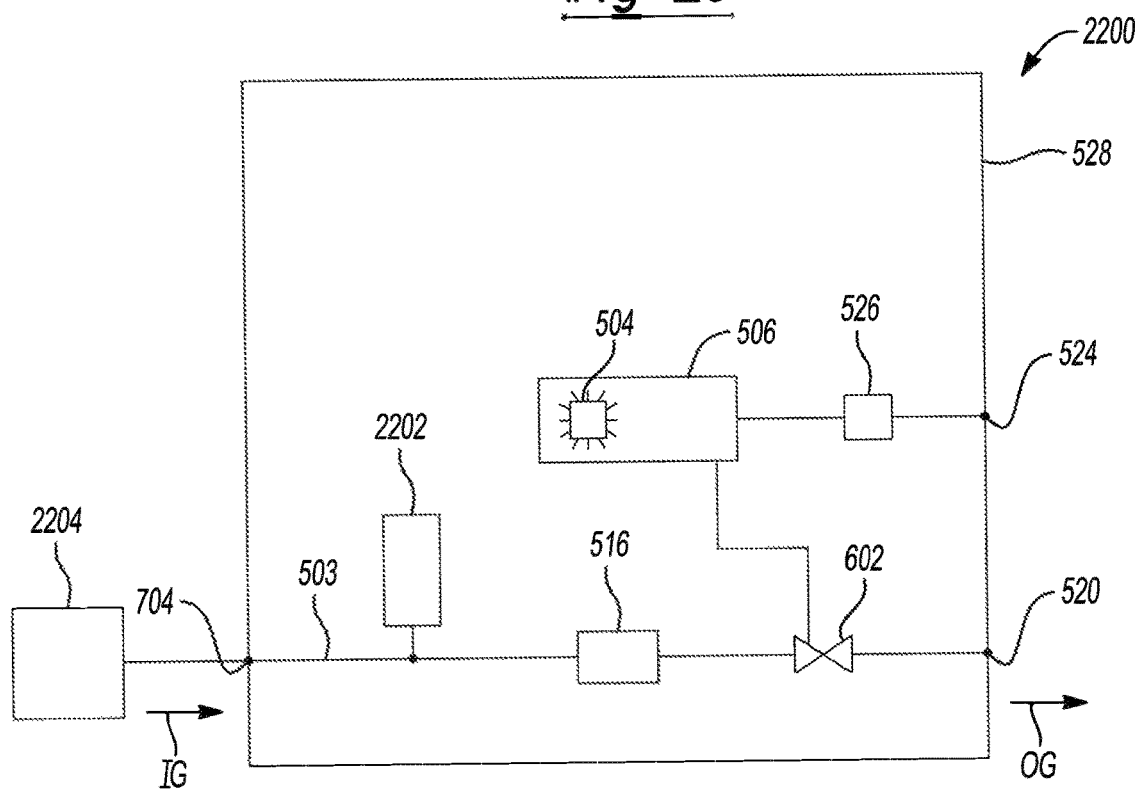
FIG. 27 is a schematic diagram of a ventilator than can use a pulse dose oxygen concentrator as an $O_2$ source.

With reference to FIG. 27, a ventilator 2200 can utilize Pulse Dose Oxygen Concentrators (POC) 2204 as the input $O_2$ source. Other ventilators can only use high pressure tanks or continuous flow stationary $O_2$ concentrators as pressure sources. This limits the mobility of these other homecare ventilators. In the present disclosure, the ventilator 2200 includes a pressure actuator 2202 that can simulate user breathing to trigger a POC oxygen concentrator 2204. During operation, the pressure actuator 2202 creates a flow ramp that would start at 0 and go past the trigger sensitivity of the $O_2$ conserver device, which may have a −0.20 $cmH_2O$ pressure trigger sensitivity. This flow ramp can be optimized based on experimental testing by the manufacturer on different POCs. Hence, a light vacuum force can be generated in order to trigger the $O_2$ conserver. This would be done at a periodic rate, such as 15 breaths or trigger cycles per minute. This periodic rate can be adjusted automatically by the controller 504 of the ventilator 2200 and/or the user via a human-computer interface to avoid the $O_2$ demanded to exceed $O_2$ produced. In some embodiments, the $O_2$ boluses from the POC can accumulate inside an air or oxygen volume tank 516. The oxygen can be stored until delivery to the patient through the valve 602. In some embodiments, these $O_2$ boluses can be measured by internal flow sensor(s) and pressure sensor(s) before accumulation into the air or oxygen volume tank 516. As such, the rate of cycling of the pressure actuator 2202 can be electronically controlled and optimized by the controller 504 based on performance of the POC input at certain breath triggering rates.

Figure 27A:
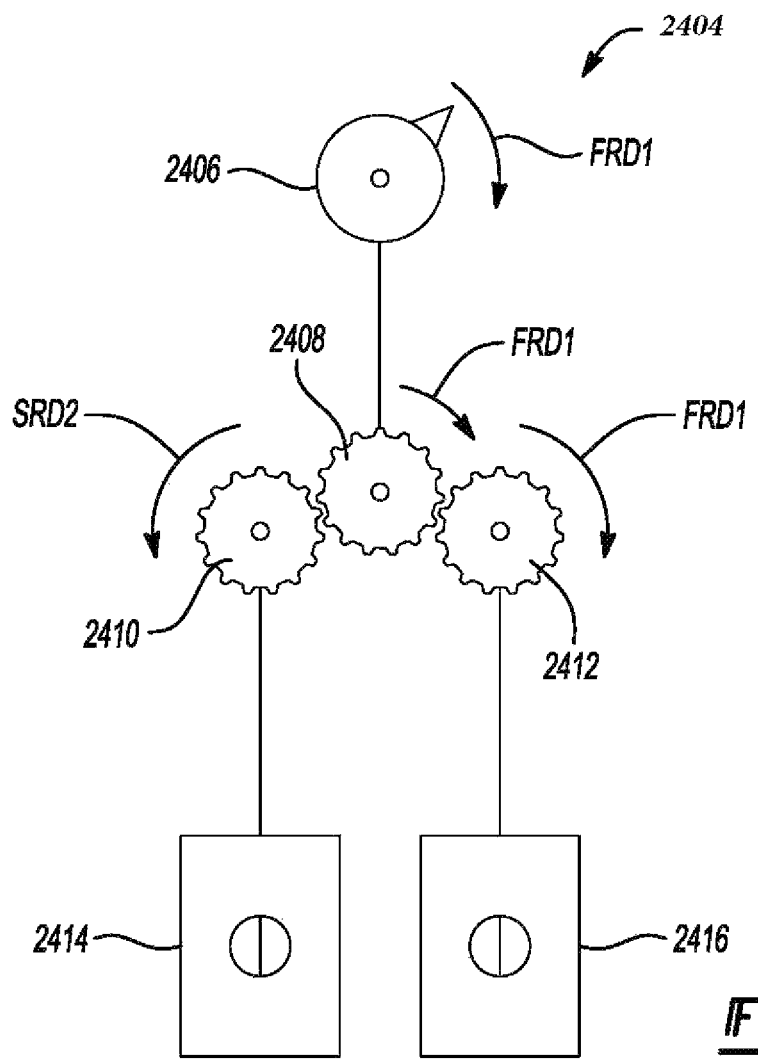
FIG. 27A is a schematic diagram of a portion of a ventilator that can allow switching between an $O_2$ concentrator and compressed air using an internal $O_2$ blower and a ball valve/gear mechanism.
Figure 27B:
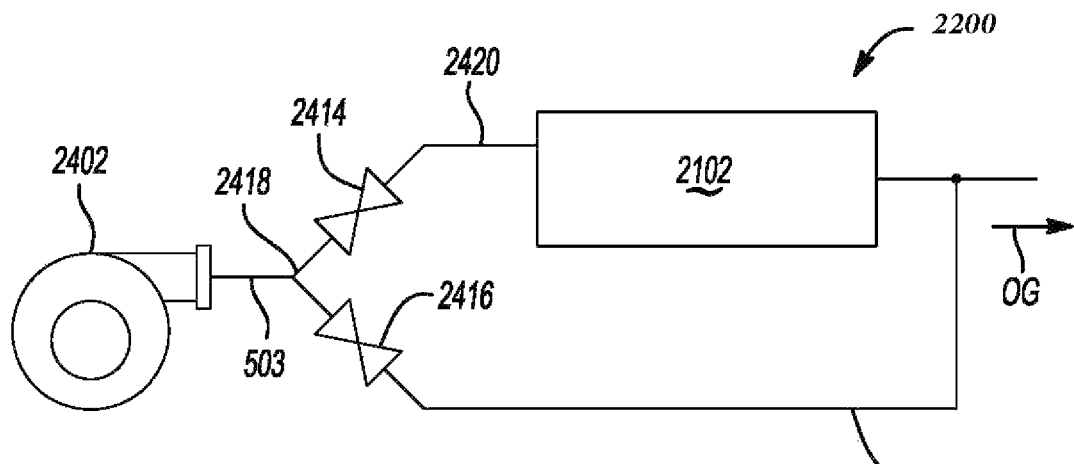
FIG. 27B is a schematic diagram of another portion of the ventilator of FIG. 27A.

With reference to FIGS. 27A and 27B, a ventilator 2200 is configured to switch between the $O_2$ concentrator 2102 and compressed air using internal $O_2$ concentrator blower 2402 and ball valve/gear mechanism 2404. In some patient cases, medical oxygen is only required in certain situations, such as during exertion or physical exercise, whereas non-invasive ventilation (NIV) or a CPAP device could be required in other situations, such as nighttime sleep, where medical $O_2$ may not be required. In this ventilator 2200, the blower 2402 is not utilized 100% of the time, and the ventilator 2200 can benefit from providing PEEP to the user with the same air compressor or blower 2402 as the internal oxygen concentrator 2102. However, the air compressor or blower 2402 can be intermittently operated with higher loading than a 100% duty due to the characteristics of the blower electric motor, which can also allow for the implementing of motor cooling systems that could further increase the performance of the blower(s) 2402 during intermittent loading. Hence, the ventilator 2200 allows switching between medical oxygen and compressed air. The ventilator 2200 includes a human-machine interface 2406 (e.g., a knob) to allow the user to manually switch the ventilator 2200 between the $O_2$ concentrator 2102 and compressed air using internal $O_2$ concentrator blower 2402 and ball valve/ gear mechanism 2404. Alternatively or additionally, the ventilator 2200 can be automatically switched between the $O_2$ concentrator 2102 and compressed air using internal $O_2$ concentrator blower 2402 and ball valve/gear mechanism 2404 using a miniature electric motor (not shown). The ball valve/gear mechanism 2404 further includes a first or middle gear 2408 coupled to the human-machine interface 2406. Activating the human-machine interface 2406 (e.g., rotating the knob) causes the first gear 2408 to rotate in a first rotational direction (such as the first rotation direction FRD1). The ball valve/gear mechanism 2404 further includes a second gear 2410 meshed with the first gear 2408. Rotating the first gear 2408 in, for example, the first rotational direction FRD1 causes the second gear 2410 to rotate in an opposite direction (for example, the second rotational direction SRD2). The ball valve/gear mechanism 2404 further includes a third gear 2412 meshed with the first gear 2408. As a consequence, rotating the first gear 2408 in, for example, the first rotational direction FRD1 causes the third gear 2412 to rotate in the same direction (e.g., the first rotational direction FRD1).

The ball valve/gear mechanism 2404 includes a first ball valve 2414 coupled to the second gear 2410 and a second valve 2416 coupled to the third gear 2412. As such, rotating the second gear 2410 causes the first ball valve 2414 to rotate to open and close, and rotating the third gear 2412 causes the second ball valve 2416 to rotate to open and close. The first ball valve 2414 and the second ball valve 2416 each have an open and closed position and an orifice sized to allow high flow low pressure gas. During operation, rotating the first gear 2408 in, for example the first rotational direction FRD1, causes the first ball valve 2414 to open while simultaneously causing the second ball valve 2416 to close. Also, rotating the first gear 2408 in the opposite direction (e.g., second rotational direction SRD2) can cause the second ball valve 2416 to open while simultaneously causing the first ball valve 2414 to close. Alternatively, rotating the third gear 2412 causes the second ball gear 2416 to open while simultaneously the rotation of the second gear 3410 (in the opposite direction) causes the first ball valve 2414 to open. The opening and closing times of the first ball valve 2414 and the second ball valve 2416 can be controlled using the gear ratios of the first gear 2408, the second gear 2410, and the third gear 24162. For example, the first ball valve 2414 and the second ball valve 2416 may open and close at the same rate. It is contemplated that one ball valve (e.g., first ball valve 2414) can always be closed, while the other one (e.g., second ball valve 2416) is open. Partial opening and closing of the first and second ball valves 2414, 2416 is also possible. As such, the ball valves (e.g., first and/or second ball valves 2414, 2416) can also be used as an orifice restriction to reduce flow rates into the internal oxygen concentrator 2102 and/or air entrainment device 522. Other types of valves could also be used including, but not limited to, gate valves, needle valves, spindle valves, check valves, and/or other types of valves not listed.

As shown in FIG. 27B, the tubing 503 of the ventilator 2200 includes a bifurcation 2418 that splits the tubing 503 into a first branch 2420 and a second branch 2422. The bifurcation 2418 is downstream of the blower 2402. The oxygen concentrator 2102 is in fluid communication with the first branch 2420 but not with the second branch 2422. The second branch 2422 bypasses the oxygen concentrator 2102. The first ball valve 2414 is disposed in the first branch 2420, and the second ball valve 2416 is disposed in the second branch 2422. The direction of the blower airflow can be controlled using these first and second ball valves 2414, 2416. For example, the ventilator 2200 can be switched to use the $O_2$ concentrator 2102 by activating the human-machine interface 2406 (e.g., rotating the knob in the first rotational direction FRD1). Such activating causes the first ball valve 2414 to open, while at the same time, causing the second ball valve 2416 to close. As a result, the airflow originating from the blower 2402 flows through the oxygen concentrator 2102 and into the patient. Alternatively, the human-machine interface 2406 can be activated to close the first ball valve 2414 and open the second ball valve 2416, causing the flow originating from the blower 2402 to bypass the oxygen concentration. As a result, the patient is provided with compressed air.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

What is claimed is:

1. A ventilator, comprising:
an enclosure;
a tubing configured to receive an input gas;
a flow outlet airline in fluid communication with the tubing, wherein the flow outlet airline includes an airline outlet, and the flow outlet airline is configured to supply an output gas to a user via the airline outlet;
a breath detection airline including an airline inlet, wherein the airline inlet is separated from the airline outlet of the flow outlet airline, and the breath detection airline is configured to receive breathing gas from the user during exhalation by the user via the airline inlet;
a pressure sensor in direct fluid communication with the breath detection airline, wherein the pressure sensor is configured to measure breathing pressure from the user, and the pressure sensor is configured to generate sensor data indicative of breathing by the user, wherein the pressure sensor is entirely disposed inside the enclosure;
a controller in electronic communication with the pressure sensor, wherein the controller is programmed to detect the breathing by the user based on the sensor data received from the pressure sensor;
a safety alarm in electronic communication with the controller, wherein the controller is programmed to generate priority warning sounds through the safety alarm based on malfunctions of the ventilator, wherein the priority warning sounds comprise a high priority warning sound, a medium priority warning sound, and a low priority warning sound;

a display interface positioned on a surface of the enclosure, the display interface in electronic communication with the controller, wherein the display interface is programmed to:
  display at least a parameter of the ventilator to a user;
  receive a user input;
  communicate the user input to the controller; and
  adjust the display of the at least a parameter based on the received user input;

an internal oxygen concentrator in fluid communication with the tubing;

wherein the oxygen concentrator is entirely disposed inside the enclosure;

a blower in fluid communication with the tubing, wherein the blower is configured to force the output gas to the user, the tubing includes a bifurcation downstream of the blower, the bifurcation splits the tubing into a first branch and a second branch, the oxygen concentrator is in fluid communication with the first branch, the second branch bypasses the oxygen concentrator.

2. The ventilator of claim 1, wherein the controller is further programmed to adjust at least a parameter of the ventilator based on the user input received from the display interface.

3. The ventilator of claim 2, wherein the at least a parameter includes a flow rate of the input gas.

4. The ventilator of claim 1, wherein the at least a parameter displayed through the display interface includes peak airway pressure sensor measurements.

5. The ventilator of claim 1, wherein the at least a parameter displayed through the display interface includes a tidal volume being delivered to a user.

6. The ventilator of claim 1, wherein the display interface is further programmed to display indications of adjustments to an input flow of the input gas.

7. The ventilator of claim 1,
  wherein the tubing, the flow outlet airline, and the breath detection airline are each at least partially disposed inside the enclosure.

8. The ventilator of claim 7, wherein the internal oxygen concentrator further comprises a zeolite adsorbent column that adsorbs nitrogen from the input gas.

9. The ventilator of claim 1, further comprising a vacuum generator in fluid communication with air inlet; and
  a bacterial filter in fluid communication with the vacuum generator, wherein the bacterial filter is positioned in an exhalation airline of the vacuum generator.

10. The ventilator of claim 1, wherein the display interface includes an LCD screen.

11. The ventilator of claim 1, wherein the display interface includes an LED screen.

12. The ventilator of claim 1, wherein the at least a parameter displayed through the display interface includes a breathing frequency of the user.

13. The ventilator of claim 1, wherein at least a parameter displayed through the display interface includes a gas source per flow rate input (LPM).

14. The ventilator of claim 1, wherein the display interface includes a touchscreen.

15. A ventilator, comprising:
an enclosure;
a tubing configured to receive an input gas;
a flow outlet airline in fluid communication with the tubing, wherein the flow outlet airline includes an airline outlet, and the flow outlet airline is configured to supply an output gas to a user via the airline outlet;
a breath detection airline including an airline inlet, wherein the airline inlet is separated from the airline outlet of the flow outline airline, and the breath detection airline is configured to receive breathing gas from the user during exhalation by the user via the airline inlet;
a pressure sensor in direct fluid communication with the breath detection airline, wherein the pressure sensor is configured to measure breathing pressure from the user, and the pressure sensor is configured to generate sensor data indicative of breathing by the user, wherein the pressure sensor is entirely disposed inside the enclosure; and
a controller in electronic communication with the pressure sensor, wherein the controller is programmed to detect the breathing by the user based on the sensor data received from the pressure sensor;
a safety alarm in electronic communication with the controller, wherein the controller is programmed to generate priority warning sounds through the safety alarm based on malfunctions of the ventilator, wherein the priority warning sounds comprise a high priority warning sound, a medium priority warning sound, and a low priority warning sound;
an internal oxygen concentrator in fluid communication with the tubing;
wherein the oxygen concentrator is entirely disposed inside the enclosure; and
a blower in fluid communication with the tubing, wherein the blower is configured to force the output gas to the user, the tubing includes a bifurcation downstream of the blower, the bifurcation splits the tubing into a first branch and a second branch, the oxygen concentrator is in fluid communication with the first branch, the second branch bypasses the oxygen concentrator.

16. The ventilator of claim 15, further comprising a first ball valve and a second ball valve, wherein the first ball valve is disposed in the first branch to control a fluid flow through the first branch, the second ball valve is disposed in the second branch to control a gas flow through the second branch.

17. The ventilator of claim 16, further comprising an air entrainment device in fluid communication with the tubing, wherein the air entrainment device is configured to entrain the input gas.

* * * * *